US006303294B1

(12) United States Patent
Emanuel et al.

(10) Patent No.: US 6,303,294 B1
(45) Date of Patent: *Oct. 16, 2001

(54) METHODS OF DETECTING GENETIC DELETIONS AND MUTATIONS ASSOCIATED WITH DIGEORGE SYNDROME, VELOCARDIOFACIAL SYNDROME, CHARGE ASSOCIATION, CONOTRUNCAL CARDIAC DEFECT, AND CLEFT PALATE AND PROBES USEFUL THEREFORE

(75) Inventors: Beverly S. Emanuel, Broomall; Marcia L. Budarf, Moylan; Deborah Driscoll, Haverford, all of PA (US)

(73) Assignees: The Children's Hospital of Philadelphia; The Trustees of the University of Pennsylvania, both of Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/473,319

(22) Filed: Jun. 7, 1995

Related U.S. Application Data

(63) Continuation-in-part of application No. 08/156,672, filed on Nov. 22, 1993, now Pat. No. 5,576,178, which is a continuation of application No. 07/911,534, filed on Jul. 10, 1992, now abandoned, which is a continuation-in-part of application No. 07/770,758, filed on Oct. 4, 1991, now abandoned.

(51) Int. Cl.⁷ .............................. C12Q 1/68; C07H 21/02
(52) U.S. Cl. ............................................. 435/6; 536/23.1
(58) Field of Search ....................... 435/6, 91.2; 536/23.1

(56) References Cited

U.S. PATENT DOCUMENTS

| 4,386,202 | 5/1983 | Nelson ................................. 544/194 |
| 4,683,195 | 7/1987 | Mullis et al. ............................ 435/6 |
| 5,576,178 | * 11/1996 | Emanuel et al. .......................... 435/6 |

OTHER PUBLICATIONS

Coullin, et al. Ann Genet 35(3): 140–145 (1992).*
Zacxai et al, Am J Hum Genet 33(6):28–31 (1981).*
Aubry, et al., "Isolation of a zinc finger gene consistently deleted in DiGeorge syndrome", *Hum. Molec. Genet., 2,* 1583–1587 (1993).
Augusseau, et al., "DiGeorge syndrome and 22q11 rearrangements", *Hum. Genet., 74,* 206 (1986).
Back, et al., "Partial Monosomy 22pter–q11 In a Newborn with the Clinical Features of Trisomy 13 Syndrome", *Ann. Genet., 23,* 244–248 (1980).
Bodenteich, et al., "Shotgun Cloning as the Strategy of Choice to Generate Templates for High–throughput Dideoxynucleotide Sequencing", *Automated DNA Sequencing And Analysis,* J. C. Venter, et al. Eds., pp. 42–50, Academic Press, London, 1993.

Botstein, et al., "Construction of a Genetic Linkage Map in Man Using Restriction Fragment Length Polymorphisms", *Am. J. Hum. Genet., 32,* 314–331 (1990).
Bowen, et al., "Thymus deficiency in an infant with a chromosome t(18;22) (q12.2; p11.2)pat rearrangement", *Clin. Genet., 29,* 174–177 (1986).
Budarf, et al., "Identification of a patient with Bernard–Soulier syndrome and a deletion in the DeGeorge/Velo–cardio–facial chromosomal region in 22q11.2", *Hum. Mol. Genet., 4,* 763–766 (1995).
Budarf, et al., "Linear Order of the Four BCR–Related Loci in 22q11", *Genomics, 3,* 168–171 (1991).
Budarf, et al., "Isolation and Regional Localization of 35 Unique Anonymous DNA Markers for Human Chromosome 22", *Genomics, 10,* 996–1002 (1988).
Carey, J.C., "Spectrum of the DiGeorge syndrome", *J. Pediatrics, 96,* 955–956 (1980).
Chissoe, et al., "Sequence and Analysis of the Human ABL Gene, the BCR Gene, and Regions Involved in the Philadelphia Chromosomal Translocation", *Genomics, 27,* 67–82 (1995).
Chissoe, et al., "Strategies for Rapid and Accurate DNA Sequencing", *Methods: Companion Methods Enzymol., 3,* 55–65 (1991).
Church, et al., "Isolation of genes from complex sources of mammalian genomic DNA using exon amplification", *Nature Genetics, 6,* 98–105 (1994).
Church and Gilbert, "Genomic sequencing", *Proc. Natl. Acad. Sci. USA, 81,* 1991–1995 (1984).
Croce, et al., "Mapping of four distinct BCR–related loci to chromosome region 22q11: Order of BCR loci relative to chronic myelogenous leukemia and acute lymphoblastic leukemia breakpoints", *Proc. Natl. Acad. Sci., 84,* 7174–7178 (1987).
Dear, et al., "A sequence assembly and editing program for efficient management of large projects", *Nucl. Acids Res., 19,* 3907–3911 (1991).

(List continued on next page.)

*Primary Examiner*—Eggerton A. Campbell
(74) *Attorney, Agent, or Firm*—Woodcock Washburn Kurtz Mackiewicz & Norris LLP

(57) ABSTRACT

There is provided by this invention methods of detecting genetic deletions, translocations, and mutations associated with at least one condition selected from the group consisting of DiGeorge syndrome, Velocardiofacial syndrome, CHARGE association, conotruncal cardiac defect, and cleft palate in a human patient comprising the steps of providing a DNA containing test sample from said human patient; identifying whether there are less than two functional copies of the DiGeorge syndrome critical region loci, whereby said identification of less than two copies of the DiGeorge syndrome critical region loci is indicative of a likelihood that said person has at least one of DiGeorge syndrome, Velocardiofacial syndrome, CHARGE association, conotruncal cardiac defect, and cleft palate. Probes and primers useful in the invention are also provided as are diagnostic kits.

12 Claims, 13 Drawing Sheets

OTHER PUBLICATIONS de la Chapelle, et al., "A Deletion in Chromosome 22 Can Cause DiGeorge Syndrome", *Hum. Genet., 57,* 253–256 (1981).

Demczuk, et al., "Cloning of a balanced translocation breakpoint in the DiGeorge syndrome critical region and isolation of a novel potential adhesion receptor gene in its vicinity", *Hum. Molec. Genet., 4,* 551–558 (1995).

Desmaze, et al., "Physical Mapping by Fish of the DeGeorge Critical Region (DGCR): Involvement of the Region in Familial Cases", *Am. J. Hum. Genet, 53,* 1239–1249 (1993).

Dobyns, et al., "Miller–Dieker syndrome: Lissencephaly and monosomy 17p", *J. Pediatr., 102,* 552–558 (1983).

Donis–Keller, et al., "A Genetic Linkage Map of the Human Genome", *Cell, 51,* 319–337 (1987).

Driscoll, et al., "A Genetic Etiology for DiGeorge Syndrome: Consistent Deletions and Microdeletions of 22q11", *Am. J. Hum. Genet., 50,* 924–933 (1992).

Driscoll, et al., "Antenatal diagnosis of DiGeorge syndrome", *Lancet, 338,* 1390–1391 (1991).

Driscoll, et al., "Molecular Analysis of DiGeorge Syndrome: 22q11 interstitial deletions", *Am. J. Hum. Genet., 47(3),* A215 (1990).

El–Fouley, et al., "DiGeorge Anomaly in an Infant with Deletion of Chromosome 22 and Dup(9p) Due to Adjacent Type II Disjunction", *Am. J. Med. Genet, 38,* 569–578 (1991).

Emanuel, et al., *The Phenotypic Mapping of Down Syndrome and Other Aneuploid Conditions,* edited by Epstein, C., Wiley–Liss, Inc., N.Y. pp. 207–224, 1993.

Faed, et al., "Features of DiGeorge syndrome in a child with 45,XX,–3,–22,+der(3), t(3;22) (p25;q11)", *J. Med. Genet., 24,* 225–234 (1987).

Feinberg and Vogelstein, "Addendum, A Technique for Radiolabeling DNA Restriction Endonuclease Fragments to High Specific Activity", *Anal. Biochem., 137,* 266–267 (1984).

Fibison, et al., "Molecular Studies of DiGeorge Syndrome", *Am. J. Hum. Genet., 46,* 888–895 (1990).

Goldberg, et al., "Phenotypic Overlap Between Velo–Cardio–Facial Syndrome (VCF) and the DiGeorge Sequence (DGS)", *Clinical Genetics, (156),* A54 (1985).

Gong, et al., "Towards a transcription map spanning a 250 kb area within the DiGeorge syndrome chomosome region (DGCR) in 22q11", *Am. J. Hum. Genet, 55,* A259 (1994).

Greenberg, "DiGeorge syndrome: a historical review of clinical and cytogenetic features,", *J. Med. Genet., 30,* 803–806 (1993).

Greenberg, et al., "Cytogenetic Findings in a Prospective Series of Patients with DiGeorge Anomaly", *Am. J. Hum. Genet., 43,* 605–611 (1988).

Greenberg, et al., "Familial DiGeorge syndrome and associated partial monosomy of chromosome 22", *Human Genet., 65,* 317–319 (1984).

Grossman, et al., "Chromosomal Mapping of the Human Catechol–O–Methyltransferase Gene to 22q11.1 q11.2", *Genomics, 12,* 822–825 (1992).

Halford, et al., "Isolation of a gene expressed during early embryogenesis from the region of 22q11 commonly deleted in DiGeorge syndrome", *Hum. Molec. Genet., 2,* 1577–1582 (1993).

Halford, et al., "Isolation of a putative transcriptional regulator from the region of 22q11 deleted in DiGeorge syndrome and familial congenital heart disease", *Hum. Molec. Genet., 2,* 2099–2107 (1993).

Kelley, et al., "The association of the DiGeorge anomalad with partial monosomy of chromosome 22", *J. Pediatr. 101,* 197–200 (1982).

Knoll, et al., "Angelman and Prader–Willi syndromes Share a Common Chromosome 15 Deletion but Differ in Parental Origin of the Deletion", *Am. J. Med. Genet., 32,* 285–290 (1989).

Kuwano, et al., "Detection of Deletions and Cryptic Translocations in Miller–Dieker Syndrome by In Situ Hybridization", *Am. J. Human Genetics, 49,* 707–714 (1991).

Lammer and Opitz, "The DiGeorge Anomaly as a Developmental Field Defect", *Am. J. Med. Genet. Supp. 2,* 113–127 (1986).

Langer, et al., "The Tricho–Rhino–Phalangeal Syndrome With Exostoses (or Langer–Giedion Syndrome): Four Additional Patients Without Mental Retardation and Review of the Literature", *Am. J. Hum. Genet. 19,* 81–111 (1984).

Ledbetter, et al., "Chromosome 15 Abnormalities and the Prader–Willi Syndrome: A Follow–up Report of 40 Cases", *Am. J. Hum. Genet., 34,* 278–285 (1982).

Lele, et al., "Chromosome deletion in a case of retinoblastoma", *Ann. Hum. Genet., 27,* 171–174 (1963).

Li, et al., "Narrowing the DiGeorge Region (DGCR) using DGS–VCFS associated translocation breakpoints", *Am. J. Hum. Genet., 55,* A10 (1994).

Litt and White, "A highly polymorphic locus in human DNA revealed by cosmid–derived probes", *Proc. Natl. Acad. Sci. USA, 82,* 6206–6210 (1985).

Mascarello, et al., "Interstitial Deletion of Chromosome 22 in a Patient With the DiGeorge Malformation Sequence", *Am. J. Med. Genet., 32,* 112–114 (1989).

McDermid, et al., "Toward a Long–Range Map of Human Chromosomal Band 22q11", *Genomics, 5,* 1–8 (1989).

McDermid, et al., "Characterization of the Supernumerary Chromosome in Cat Eye Syndrome", *Science, 232,* 646–648 (1986).

Nisson, et al., *Current Protocols in Human Genetics, vol. I,* Drapacoli, N.C., et al., Eds., pp. 6.1.1–6.1.14, John Wiley & Sons, N.Y. (1994).

Pivnick, et al., "Adjacent–2 Disjunction of a Maternal t(9;22) Leading to Duplication 9pter—>q22 and Deficiency of 22pter—>q11.2", *Am. J. Med. Genet., 37,* 92–96 (1990).

Pulver, et al., "Sequential Strategy to Identify a Susceptibility Gene for Schizophrenia: Report of Potential Linkage on Chromosome 22q112–Q13.1: Part I", *Am. J. Med. Gen., 54,* 36–43 (1994).

Riccardi, et al., "Chromosomal Imbalance in the Aniridia–Wilms' Tumor Association: 11p Interstitial Deletion", *Pediatrics, 61,* 604–610 (1978).

Rouleau, et al., "A Genetic Linkage Map of the Long Arm of Human Chromosome 22", *Genomics, 4,* 1–6 (1989).

Scambler, et al., "Microdeletions within 22q11 Associated with Sporadic and Familial DiGeorge Syndrome", *Genomics, 10,* 201–206 (1991).

Schnizel, "Microdeletion syndromes, balanced translocations, and gene mapping", *J. Med. Genet., 25,* 454–462 (1988).

Schmickel, et al., "Contiguous gene syndromes: A component of recognizable syndromes", *J. Pediatr., 109,* 231–241 (1986).

Shprintzen, et al., "A New Syndrome Involving Cleft Palate, Cardiac Anomalies, Typical Facies, and Learning Disabilities: Velo–Cardio–Facial Syndrome", *Cleft Palate J.*, 5, 56–62 (1978).

Shprintzen, et al., "The Velo–Cardio–Facial Syndrome: A Clinical and Genetic Analysis", *Pediatrics.*, 67, 167–172 (1981).

Shprintzen, et al., "The Expanded Velo–Cardio–Facial Syndrome (VCF): Additional Features of the Most Common Clefting Syndrome", *Am. J. Human Genet.*, 37, A77 (1985).

Southern, "Detection of Specific Sequences Among DNA Fragments Separated by Gel Electrophoresis", *J. Mol. Biol.*, 98, 503–517 (1975).

Spinner, et al., "Cytologically Balanced t(2;20) in a Two-Generation Family with Alagille Syndrome: Cytogenetic and Molecular Studies", *Am. J. Hum. Genet.*, 55, 238–243 (1994).

Stevens, et al., "DiGeorge anomaly and relocardiofacial syndrome", *Pediatrics*, 85, 526–530 (1990).

Stratton, et al., "New chromosomal syndrome: Miller–Dieker syndrome and monosomy 17p13", *Human Genet.*, 67, 193–200 (1984).

Uberbacher, et al., "Locating protein–coding regions in human DNA sequences by a multiple sensor–neural network approach", *Proc. Natl. Acad. Sci. USA.*, 88, 11261–11265 (1991).

Verga, et al., "Localization of the Translocation Breakpoint in a Female with Menkes syndrome to Xqq13.2–q13.3 Proximal to PGK.I", *Am. J. Hum. Genet.*, 48, 1133–1138 (1991).

Williams, et al., "Male–to–Male Transmission of the Velo–Cardio–Facial Syndrome: A Case Report and Review of 60 cases", *J. Craniofacial Genet.*, 5, 175–180 (1985).

\* cited by examiner

FIG. 3
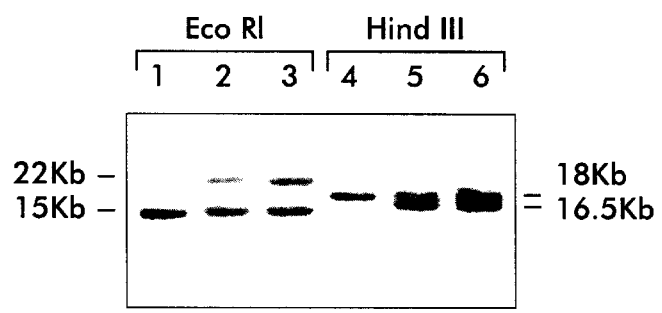
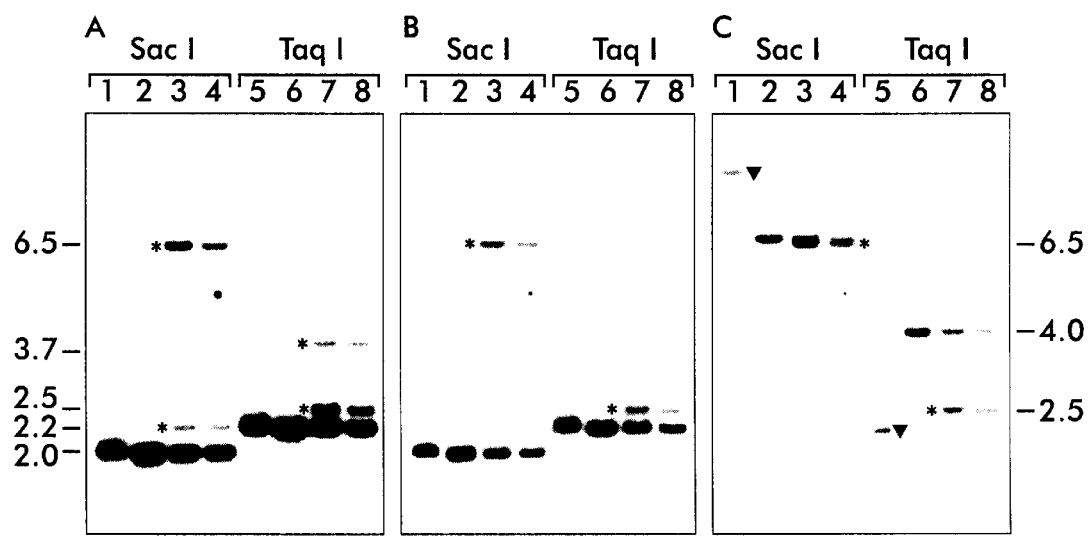
FIG. 5

|  |  |  |  |  |  |
|---|---|---|---|---|---|
| 1 | GATCCTGCGT | AAGTGTGGAG | GCTGGAGTGC | ATGCCTTGGG | GATGCCGGAG | CCTAGCTGTG |
| 61 | CTCGGTGAGA | GGGAGGCTGC | AGGGAAGGAG | GATCGGGATG | CCGGTGGAGC | TGCTTGATCC |
| 121 | TCTGAAGACA | GGAGGCCATT | GAGGGCGCTT | CCACGGGGAT | TGGTGAGACC | AGATCCAAGT |
| 181 | ACCAAAAGCA | TCATTCTGGG | GACCAGGACT | GGAAGGGGAG | GCTGGATAAA | CAGCTCAGGG |
| 241 | GAGGAACAGA | AGGGCCAGAA | GATAGATGGA | TGCGTAGTTT | CCCCGCCCAG | CAATGTCGCC |
| 301 | ACCTGGCTGT | GCGCTGCACC | CTCAGTTTCC | CCATCTGTGA | AGGGGGATT | GCCCTGAGGG |
| 361 | ATCTTAGTAG | CCCCTCCCGC | TCCGAGATGC | TGCAGCACTC | CTCTCTGGGC | CCCCACACAG |
| 421 | CTTTGCCTCT | CAGGCCAGCC | CTTGGAAACG | ATGCTGGGTG | AGGCTTGGAG | GGTTTCAGGA |
| 481 | GGAAGGGTTT | CTGAGTGACC | CTGCCACCCC | GTGAGTTATT | TGCAATGGCT | ACAACTGAGG |
| 541 | GGCCGTAGAA | TCTGGCTTCT | GTGAGTTATT | CCATTAATAT | TCCCTCCAGG | AAGCTTTGCC |
| 601 | AGACAGGGAG | GAGGCAGGGG | GCAGATGGGG | CACTGAGAGG | CCAAGTAATC | TGCTTAAGGT |
| 661 | CACCCAGCAA | AGCAGCAGCA | AGCTGGACCG | GGCCCCAGGC | CTCCAGATGT | CCAGTCTGAT |
| 721 | GCCCTGCCCA | CTGGACCCA | AGGCCTTTAA | TGAGCCCACC | TCCATGGGGG | CTGTGGGCTG |
| 781 | GCCCACCCGC | CAGGCCATG | GACTTGCCAG | GCATCCCAAT | CAGCCACTCC | GGAGAGGCCC |
| 841 | TGCCCTTGGC | GGCCATGCAC | AGAGGCTGG | TGTGAGCATG | CCAGCTGAGA | CTGGAGGCTC |
| 901 | TGCAAGGTAG | CCCCTAGGTC | TGAGCATGCC | CAACCCTCCA | TCCAGGACCC | CTGAGGAACA |
| 961 | GGGTTCTACA | TCCAGAAAGA | GGCCAGCCAC | GTCTCAGGGG | CTGGGGTGCT | GCAGGCATCA |
| 1021 | TCACTCACAG | GTCCTCCAAG | CTGGGCCCTG | GCACCTGGGC | CAGGGTCCTG | GGGGATGAC |
| 1081 | CCCAGCCCGC | TTGAGCTGCT | GAATTTGCAG | TGCGTGTTGC | TGGCATCCAT | GGCCAGCACT |
| 1141 | GTCTGCCTCT | ATACTCCATT | CCGGAGCCCA | ACAACACAGA | GAGCCAGGGC | CCCCTGCACC |
| 1201 | CAGCCCTTCA | TGGACAGAAG | AAGGCAGGGC | GTGTCAGAGG | TGCATGGTGA | GGGCCTGGGT |
| 1261 | CACATGGGA | GATGGTGAAA | TCAAATAGGG | TCTCCTGCT | GGGCAGGACT | TCCAGGCCAG |
| 1321 | CTTCCTGCAT | TGCCCTATAA | AGTCTCAGCT | TTGTCTTCAT | CCTAATAACA | CCTGGAAAAG |
| 1381 | CCACCTCCGC | TGAGCCATAA | CCAGGACCCA | TGGGCACTGG | CTGAG |  |

SEQ ID NO.: 28

```
   1  CAGAGATCAC AAAACTAACA GCTCTTTCTG CAAATCTGGA CTCTCTCCTG CACCTTCTTC
  61  ACCGTCCAGG CCTCCCTGTC ATCCGTCCTG GGGACCTCAG AGATCTCTTC ATTTCACAGG
 121  TGAAGACTTG GCTCAGAGAG GGCAGAGCCC CTGGGTCACA CAGCCCGTCT CCAGTAGGGC
 181  TGGGGAAAAG AACCCAGGGC GCTCTTGTTG GCAGTGTTTT AATGACTGGG GGGAGGGAGA
 241  GAATGGCTAA TGAGGCTCTA GGGATCAGCA CAGCCAGCTG CTGGAGGTCC CAGAGGACGG
 301  GTGACTCAGC AGGAATGGGG GAGTCTGAGG GGTTGACAGA GTGCCCAATT CTCACCTCT
 361  CCTGCACCTT CCAGAGAGAC GGGCTGCAGG GAGTGATTGA GTGGATGAAC ATGACTAGAG
 421  GGACCCAGTC TTCTCCTCAG CAGCTGCTTG AGGACAGTAT TAGCGGTCCC CTCAATCCCC
 481  CCCCAACAC ATGCACACAT GCACTGACCT GCAGGGGCCA GATCCCGGTG GACCCGGGGA
 541  CACAGCTTCC AGGGGCTGTC TTGCCCATGT CCCTTCCCAGA TCTGCCCTGA TTCATGCCAG
 601  GCCACCCTCC ACAATTTGCT GAGGGAGGCC CCAGAGTCCA GGGCACCCAG AGTGCTAACT
 661  AGCCCCTGGG GGTACAGGGA GAACAGCATG CTGTGTGGGG GATACTACTC TCTGCCCATA
 721  CCTAGGGCCC TGTGGCGGCC ACAGCCAGCA CTGCTTATGC AGAGGCACTG GGGTGAGAAG
 781  GAGTAGGGTG CAGTAGTGAG GGCTCCACAG AGGGTGGAAG GGCTGCAGGG GAAGGCAGAC
 841  CAGCAGGGAT GCCAAGAGGG CCTCAGATGC CAGGCTGCAG AGGTGGACGG GCTGGCCAGC
 901  TCCTCTCCCC AGCCTCCTAC TGTAAAATGG GAGAGGATCC CAGCCCTGCT GATTCATCCA
 961  CTCACTCCAT GGCAAGACAG CCACTGACAG CTCTGTCCTG GGCCCACCC GGGCCTGGCC
1021  TCTGTGCAGG CTAGCACTCA GTATGCTTAG CCACTGACAC TGCCCACACTC AAATGACCCA
1081  GCCCTGGGCT CAGAGACCCC ACAGTGGGTG GATGGAAAAC AGTCATTTAA ATACAACTGT
1141  GAAGGGTGCT GTGGAGGAGG GGCTCGAGGT CCCCAGTGTG GGATGGGGTG GTCATGGAAC
1201  GTTTCCCTAT CTAAGTGGGA AAAGTGAGAG CCACCAGGAA AATGGCGGGG GTGGGGGGG
1261  AGAGGAATTA TGCAAAGACC CAGAAGGATG CAGAAGACTG AAGAAGACTG TTGGATTAGA GGAGGTTAAA
```

SEQ ID NO.: 29

FIG.6C chr 2:
CCAGAAAGAGGCCCAGCCACGTCTCCAGGGGCTGGGGTGctgcaGGCATCATCATCACTCACAGGTCCTCCAAGCTGGG   SEQ ID NO.: 30 der 2:
CCAGAAAGAGGCCCAGCCACGTCTCCAGGGGCTGGGGTG   SEQ ID NO.: 31

CATCATCACTCACAGGTCCTCCAAGCTGGG

ATTGAGTGGATGAACATGACTAGAGG   SEQ ID NO.: 32 der 22:
ATTCTCACCTCCCTGCACCTTCCAGAGAGACGGGCTGCAGGG chr 22:
ATTCTCACCTCCCTGCACCTTCCAGAGAGACGGGCTGCAGGGaGTGATTGAGTGGATGAACATGACTAGAGG   SEQ ID NO.: 33

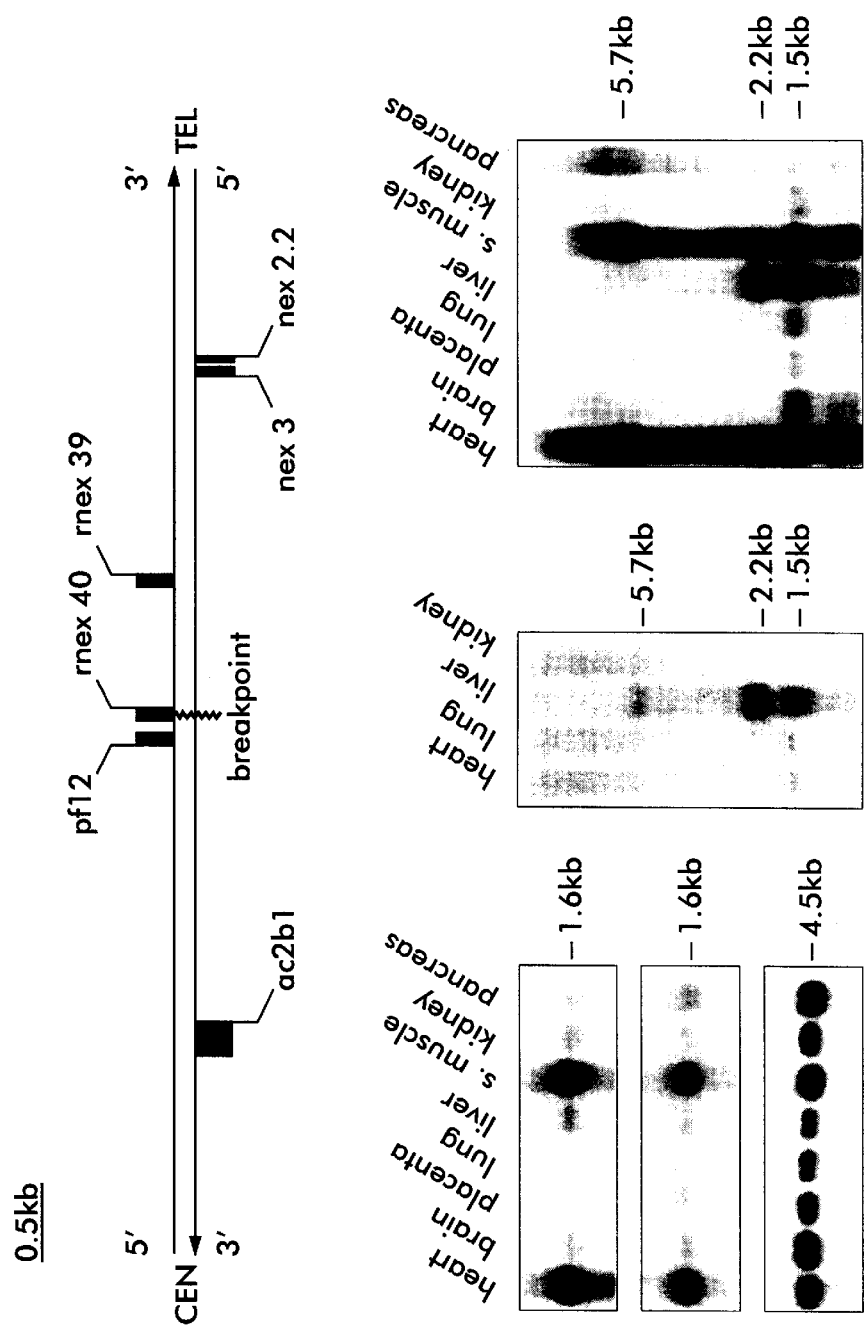

FIG.9A

```
  1  L  W  N  P  L  P  Q  V  P  A  P  T  S  V  A  P  A  G  T  S
     CTTGGAACCCTCTGCCCAAGTGCCACACATCTGTAGCCCCTGCAGGAACAAGC
 21  P  N  L  D  S  L  Q  W  L  S  F  S  S  N  L  S  I  N  L  Q
     CCTAATCTGGACTCATTGCAATGGCTCAGCTTCTTCCAACCTGTCCATAAACCTCCAG
 41  A  E  I  T  K  L  T  A  L  S  A  N  L  D  S  L  L  H  L  L
     GCAGAGATCACAAAACTAACAGCTCTTTCTGCAAATCTGGACTCTCTCCTGCACCTTCTT
 61  H  R  P  G  L  P  V  I  R  P  G  D  L  R  D  L  F  I  S  Q
     CACCGTCCAGGCCTCCCTGTCATCCGTCCTGGGACCTCAGAGATCTTCATTTCACAG
 81  V  K  T  W  L  R  E  G  R  A  P  G  S  H  S  P  P  V  G
     GTGAAGACTTGGCTCAGAGAGGGCAGAGCCCCTGGGTCACACAGCCCGTCTCCAGTAGGG
101  L  G  K  R  T  Q  G  A  L  V  G  S  V  L  N  T  G  G  R  E
     CTGGGGAAAGAACCCAGGGGCGCTCTTGTTGGCAGTGTTTTAATGACTGGGGGAGGAG
121  R  M  A  N  E  A  L  G  I  S  T  A  S  C  W  R  S  Q  R  T
     AGAATGGCTAATGAGGCTCTAGGGATCAGCACAGCCAGCTGCTGGAGGTCCCAGAGGACG
141  G  D  S  A  G  M  G  E  S  E  G  L  T  E  C  P  I  L  T  S
     GGTGACTCAGCAGGAATGGGGGAGTCTGAGGGTTGACAGAGTGCCCAATTCTCACCTCC
161  S  C  T  F  Q  R  D  G  L  Q  G  V  I  E  W  M  N  M  T  R
     TCCTGCACCTTCCAGAGAGACGGGCTGCAGGGAGTGATTGAGTGGATGAACATGACTAGA
                                            ┌─────────────────────────┐
                                            │ I  I  T  H  R  S  K  L  │
                                            │ CATCATCACTCACAGTCCTCCAAGCTG │
                                            └─────────────────────────┘
```

```
181  G  T  Q  S  S  P  Q  Q  L  L  E  D  S  I  S  G  P  L  N  P
     GGGACCCAGTCTTCTCCTCAGCAGCTGCTTGAGGACAGTATTAGCGGTCCCCTCAATCCC
     GGCCTCGGCACCTGGGCCAGGGTCCTGGGGGATGA  —
     G  L  G  T  W  A  R  V  L  G  G   —

201  P  P  N  T  C  T  H  A  L  T  C  R  G  Q  I  P  V  D  P  G
     CCCCCAACACATGCACACACTGACCTGCAGGGCCAGATCCCGGTGGACCCGGGG

221  T  Q  L  P  G  A  V  L  P  C  P  F  P  D  L  P  G  F  M  P
     ACACAGTTCCAGGGCGCTGTCTTGCCATGTCCCTTCCCAGATCTGCCTGGATTCATGCCA

241  G  H  P  P  Q  F  A  E  G  G  P  R  V  Q  G  T  Q  S  A  N
     GGGCCACCCTCCACAATTTGCTGAGGAGGCCCCAGAGTCCAGGCACCCAGAGTGCTAAC

261  —
     TAG

SEQ ID NO.: 34
SEQ ID NO.: 35
```

```
rat   AR  101  aseghpespclPepgAatapgkglpqqppappdqdDSaa......pStLSl.LgptfpgLss
mouse AR  101  aseghpesSclPepgAatapgkglpqqppappdqdDSaa......pStLSl.LgptfpgLss
human AR  120  aLeChpeRGcVPepgAavaASkglpqqLpappd dDSaa......pStLSl.LgptfpgLss
rnex40      1                    LWNPlPQVPAPtSVA......pAGTSPNLDSLQWLSFSSNLSINLQAEITKLTA rat   AR  156  cSAdikdiLseagtmgLLQQqqqqqqqqOqqqqqevi SegsssVRareAtGaps
mouse AR  156  cSAdikdiLNeagtmqLL..qqqqqqHqqHqqqevi SegsssA.RareAtGaps
human AR  175  cSAdLkdiLseaStmqLL...........qqqqqeAVSegsssGRareASGapT
rnex40     49  LSANLDSLL.......HLL.........HRPGLPVIRPGDLRDLFiSQVKTWLREGRAPGSHs rat   AR  216  sSkdsylggnstisdsakelckavsvsmGLGvealehlspgeqlrgdcmyaslLggpppav
mouse AR  213  sSkdaylggnstisdsakelckavsvsmGLGvealehlspgeqlrgdcmyaslLggpppav
human AR  218  sSkdNylggTstisdNakelckavsvsmGLGvealehlspgeqlrgdcmyaPlLGvVppav
rnex40     96  PS..................PVGLGKRT.......QGALVGSVL......
```

FIG. 9D

```
rat   AR  276  rptpcaplaeckglSldegpGkGTeetaeyssfkgGyakGleGESlGcsgsseagSSgTl
mouse AR  273  rptpcaplPeckglPldegpGksTeetaeyssfkgGyakGleGESlGcsgsseagSSgTl
human AR  278  rptpcaplaeckgSLldDSAGksTeDtaeysPfkgGyTkGleGESlGcsgsAAagSSgTl
rnex40    115  ........MTGGRERMANeAlGiSTASC..WRsQRTGDSAGM.GESEGLTECPILTSSCTF rat   AR  336  eipsslslyksgaVdeaaayqnrdyynfplalsGPphPPPpthpHA..riklenPlDyGsa
mouse AR  333  eipsslslyksgaldeaaayqnrdyynfplalsGPphPPPpthpHA..riklenPlDyGsa
human AR  338  eLpsTlslyksgaldeaaayqSrdyynfplalAGPpPPPPphpHA..riklenPlDyGsa
rnex40    165  QRDGLQGVIEWMXMXRGTQSSPQQL..LEDSISGPLNPPPNtCTHALTCRGQIPVDPGTQ
                        * rat   AR  395  waaAaaqCrygDLaslhggsvagpstGsPpatassSwhtlftaeeggqlygp........
mouse AR  392  waaAaaqCrygDLGslhggsvagpstGsPpatTssSwhtlftaeeggqlygp........
human AR  397  waaAaaqCrygDLaslhgAGAagpGSGsPSaAasssSwhtlftaeeggqlygpCGGGGGG
rnex40    223  LPGAVLPCPFPDLPGFMPgHPPQFAEGGPRVQGTQSAN*
```

METHODS OF DETECTING GENETIC DELETIONS AND MUTATIONS ASSOCIATED WITH DIGEORGE SYNDROME, VELOCARDIOFACIAL SYNDROME, CHARGE ASSOCIATION, CONOTRUNCAL CARDIAC DEFECT, AND CLEFT PALATE AND PROBES USEFUL THEREFORE

CROSS REFERENCE TO RELATED APPLICATIONS

This application is a continuation-in-part of application Ser. No. 08/156,672 entitled "Methods of Diagnosing DiGeorge Syndrome, Velocardiofacial Syndrome, Charge Association, and Conotruncal Defect, filed Nov. 22, 1993, now U.S. Pat. No. 5,576,178, which is a continuation of application Ser. No. 07/911,534, filed Jul. 10, 1992, now abandoned, which is a continuation-in-part of application Ser. No. 07/770,758, filed Oct. 4, 1991, now abandoned, incorporated by reference herein in its entirety.

REFERENCE TO GOVERNMENT GRANTS

The work present herein was supported in part by National Institute of Health grants CA 39926, HG00425, HL51533, DC02027, and HD26979 and from the Reproductive Scientist Training Program (D.A.D.). The United States government has certain rights in the invention.

FIELD OF THE INVENTION

The present invention relates to the field of human diagnostics. More particularly, the invention relates to the detection of genetic deletions and mutations associated with DiGeorge Syndrome (DGS) and related syndromes of Velocardiofacial (Shprintzen) syndrome, CHARGE association, conotruncal cardiac defect, and cleft palate in humans using probes within the common region of overlap for substantially all deletions and mutations associated with these diseases.

BACKGROUND OF THE INVENTION

DiGeorge syndrome (DGS) is a developmental field defect of the third and fourth pharyngeal pouches characterized by thymic aplasia or hypoplasia, absent or hypoplastic parathyroid glands and conotruncal cardiac malformations. The etiology is presumed to be heterogenous with reported cases demonstrating autosomal dominant, autosomal recessive, X-linked and chromosomal modes of inheritance (Lammer and Opitz, (1986) *Am J. Med. Genet.* 2:113–127). Approximately 15–20% of patients with DGS have detectable chromosomal abnormalities (Greenberg, et al. (1988) *Am. J. Hum. Genet.* 43: 605–611). There are several examples of specific associations between chromosomal deletions and diseases, including Prader-Willi syndrome (Ledbetter et al. (1982) *Am. J. Hum. Genet.* 34: 278–285), Langer-Gideon syndrome (Langer et al. (1984), *Am. J. Med. Genet.* 19: 81–111), Miller-Dieker syndrome (Dobyns et al., (1983), *J. Pediatr* 102: 552–558; Stratton et al.,(1984), *Human Genet* 67: 193–200) the aniridia-Wilms tumor association (Riccardi et al, (1978), *Pediatrics* 61: 604–610), and retinoblastoma (Lele et al. (1963), *Ann. Hum Genet* 27: 171–174). DiGeorge syndrome has been linked to chromosomal deletion of chromosome 22. All of these syndromes have been analyzed using molecular techniques (reviewed by Schinzel (1988), *J. Med. Genet,* 5: 454–462). DGS has many of the characteristics associated with this group of deletions syndromes, which have been referred to by Schmickel (1986), *J. Pediatr.* 109: 231–241, as "contiguous gene syndromes". These syndromes tend to be relatively rare, are often sporadic, and have few examples where the disorder is familial. Patients show variation in the severity of their associated symptoms and often manifest additional phenotypic features, possible reflective of the number of genes involved. The majority of cytogenetically abnormal cases of DGS reported involved chromosome 22 and result from malsegregation of a familial balanced translocation leading to monosomy 22pter→22q11 (Back et al. (1980), *Ann. Genet.* 23: 244–288; de la Chapelle et al. (1981), *Hum Genet.* 57: 253–256; Kelley, et al. (1982) *J. Pediatr.* 101: 197–200 (1982); Greenberg et al., (1984), *Human Genet.* 65: 317–319; Greenberg et al. (1988) *Am. J. Hum. Genet.* 43: 605–611; Augusseau, et al. (1986) *Hum. Genet* 74: 206; Bowen et al., (1986), *Clin. Genet.* 29: 174–177; Faed, et al. (1987), *J. Med/Genet* 24: 225–234 (1987). Two patients have been reported with interstitial deletions, del(22) (q11.21→q11.23) (Greenberg et al. (1988), *Am. J. Human Genet* 43: 605–611; Mascarello et al. (1989), *Am. J. Med. Genet* 32: 112–114; El-Fouley et al. (1991), *Am J. Med. Genet* 38: 569–578 and Driscoll, et al. (1992), *Am. J. Hum Genet.* 50: 924–933. Based on cytogenetic studies, it has been hypothesized that the deletion of contiguous genes located on chromosome 22 results in DGS and that the region critical to DGS (DGCR) lies in 22q11. (de la Chapelle et al.,(1981), *Hum. Genet* 57:253–256; Kelley et al., (1982), *J. Pediatr.* 101: 197–200; Schmickel, (1986), *J. Pediatr.* 109: 231–241). The description of a DGS-associated region within 22q11 which invariably involves codeletion of loci D22S75, D22S66 and D22S259 has begun to delineate the DiGeorge syndrome chromosome region (DGCR), hereinafter referred to as the DiGeorge Critical Region (Driscoll et al (1992), *Am J. Human Genet.* 50: 924–933.

Velo-cardio-facial syndrome (VCF) is an autosomal dominant disorder characterized by cleft palate, cardiac defects, learning disabilities and a typical facial dysmorphism (Shprintzen et al. (1978), *Cleft Palate J.* 15: 56; Spprintzen et al. (1981), *Pediatr.* 67: 167–172 and Williams et al. (1985), *J. Craniofacial Genet* 5: 175–180). Additional features have been described including microcephaly, short stature, inguinal and umbilical hernias, Robin sequence, scoliosis, platybasia, ophthalmologic abnormalities, neonatal hypocalcemia and decreased lymphoid tissue (Shprintzen et al. (1985), *Am J. Human Genet* 37: A77; Williams et al, (1985) *J. Craniofacial Genet.* 5: 175–180). The presence of neonatal hypocalcemia, absent or hypoplastic lymphoid tissue and T-cell dysfunction, which are features of DiGeorge syndrome (DGS), suggests that DGS and VCF may share a common pathogenesis (Goldberg et al. (1985), *Am. J. Hum. Genet.* 37: A54). Review of previously reported DGS cases with autosomal dominant transmission suggests that these families actually have clinical features more consistent with the diagnosis of VCF (Lammer and Opitz, (1986), *Am. J. Med. Genet.* 29: 113–127; Stevens et al. (1990), *Pediatrics* 85: 526–530. Based on the phenotypic overlap between DGS and VCF, it is believed that VCF could be caused by deletion of genes from within the DGCR or from a partially overlapping region.

CHARGE association is a condition in which the abnormalities which constitute DGS also play a significant role. Conotruncal cardiac defects are a spearate condition in which deletions of 22q11 have been shown to play a significant role.

Even high resolution cytogenetic studies are not always adequate to detect genetic deletions associated with conditions such as DGS, VCF and related conditions such as CHARGE association, conotruncal defect, cleft palate. In many cases deletions within chromosome 22 are molecular deletions which may only be detected by means of molecular studies. Large molecular deletions can be detected for example, by restriction fragment length polymorphism (RFLP) analysis using several anonymous DNA markers located within the DGCR. However, RFLP studies are not always fully informative. In the past, studies of uninformative patients involved segregation of maternal and paternal homologs of chromosome 22 into different somatic cell hybrids. However, the construction of somatic cell hybrids is labor intensive and is not practical as a routine diagnostic tool. A fast and efficient method for detecting conditions associated with deletions, mutations, and translocations involving chromosome 22 such as are seen in DGS, VCF, CHARGE association, conotruncal defect, and cleft palate is greatly needed.

Probes to deletion and translocation regions have been used diagnostically. For example, fluorescence in situ hybridization (FISH) utilizing cosmid probes from the 17p13.3 region has been used to identify submicroscopic deletions and to define cryptic translocations in patients with Miller-Dieker syndrome (Kuwano et al. (1991), *Am J. Human Genetics,* 49: 707–714).

Therefore, probes directed to the DiGeorge syndrome critical region are greatly desired to enhance the detection of genetic deletions and mutations associated with DiGeorge syndrome and the related conditions of Velocardiofacial syndrome, CHARGE association, conotruncal cardiac defect and cleft palate. Diagnosis of a deletion or mutation will permit the clinician to provide the proband as well as the family with an accurate assessment of the recurrence risk and to offer prenatal monitoring for the detection of a deletion in subsequent pregnancies. In addition to the use of ultrasonography and fetal echocardiography for the detection of cleft palate and congenital heart defects, amniocentesis or chorionic villus sampling can be utilized for the cytogenetic, fluorescence in situ hybridization (FISH) and molecular evaluation of the fetus for 22q11 deletions and mutations (Driscoll et al (1991) *Lancet* 338: 1390–1391).

SUMMARY OF THE INVENTION

There is provided by this invention novel methods of detecting genetic deletions, translocations, and mutations associated with at least one condition selected from the group consisting of DiGeorge syndrome, Velocardiofacial syndrome, CHARGE association, conotruncal cardiac defect, and cleft palate in a human patient. The method comprising the steps of providing a DNA containing test sample from said human patient; identifying whether there are less than two functional copies of the DiGeorge syndrome critical region loci, whereby said identification of less than two functional copies of the DiGeorge syndrome critical region loci is indicative of a likelihood that said person has a genetic deletion or mutation associated with at least one condition selected from the group consisting of DiGeorge syndrome, Velocardiofacial syndrome, CHARGE association, conotruncal cardiac defect and cleft palate. The method according to the invention further comprises the identification of a balanced translocation in the DGCR associated with the foregoing conditions.

In another aspect of the invention there is provided novel methods of preparing diagnostic probes useful for the detection of genetic deletions, translocations, and mutations associated with at least one condition selected from the group consisting of DiGeorge Syndrome, Velocardiofacial syndrome, CHARGE association, conotruncal cardiac defect, and cleft palate. The invention comprises the steps of preparing primer pairs effective to amplify a region of chromosome 22q11 shown to be unique sequences in the DiGeorge syndrome critical region, or a region of chromosomes der(2) and der(22) from patients identified as having the translocation described herein; synthesizing DNA substantially complementary to a region of normal human genomic DNA or cDNA by PCR amplification using said primer pairs; and isolating a DiGeorge syndrome critical region probe. For the detection of deletions or mutations, the probes can be isolated from a library containing human chromosome 22 using said substantially complementary DNA. In preferred embodiments the primers are selected from the group consisting of 5'ACACTGGTCCACAGT-GCCAG3' (SEQ ID NO:1) and 5'TGTGAGGGCT-TGCTCTGAGC3' (SEQ ID NO: 2); 5'TGGTACCGCT-GCTCAGAGGGC3' (SEQ ID NO:3) and 5'TCCCAGCCTCTGGCCTGAGTG3' (SEQ ID NO: 4); and 5'CTAACACCTATCCTCCGCCG3' (SEQ ID NO: 5) and 5'GGCAGCAGGGAAACAGAAAC3' (SEQ ID NO: 6); Also provided by the invention are the probes produced thereby.

For the detection of the translocation herein described, the probes can be isolated from probes identified near the t(2;22).

In yet another aspect of the invention there is provided novel diagnostic probes useful for the detection genetic deletions, translocations, and mutations associated with at least one condition selected from the group consisting of DiGeorge syndrome, Velocardiofacial syndrome, CHARGE association, conotruncal cardiac defect and cleft palate. These methods comprise PCR amplifying clones from libraries containing chromosome 22 to identify clones containing the probes. Also provided by the invention are the probes produced thereby.

There is further provided by the invention diagnostic kits for the detection of a genetic deletion, translocation, or mutation associated with at least one condition selected from the group consisting of DiGeorge syndrome, Velocardiofacial syndrome, CHARGE association, conotruncal cardiac defect and cleft palate comprising a diagnostic probe selected from the group consisting of probes prepared by methods of this invention or primer pairs effective to amplify a region of chromosome 22q11 shown to be unique sequences in the DiGeorge syndrome critical region.

These and other aspects of the invention will become more apparent from the following detailed description when taken in conjunction with the following drawing.

BRIEF DESCRIPTION OF THE DRAWINGS

FIG. 3 depicts the detection of rearrangement fragments with the LAN cDNA.

FIGS. 4A–4B depicts restriction maps of the breakpoint regions.

FIG. 5 depicts the mapping of the t(2;22) translocation breakpoint.

FIGS. 8A–8F depicts the transcript map and northern blot analysis of the breakpoint region.

FIGS. 9A–9D depicts the sequence of the predicted protein disrupted by the t(2;22).

DETAILED DESCRIPTION OF THE INVENTION

Figure 1:
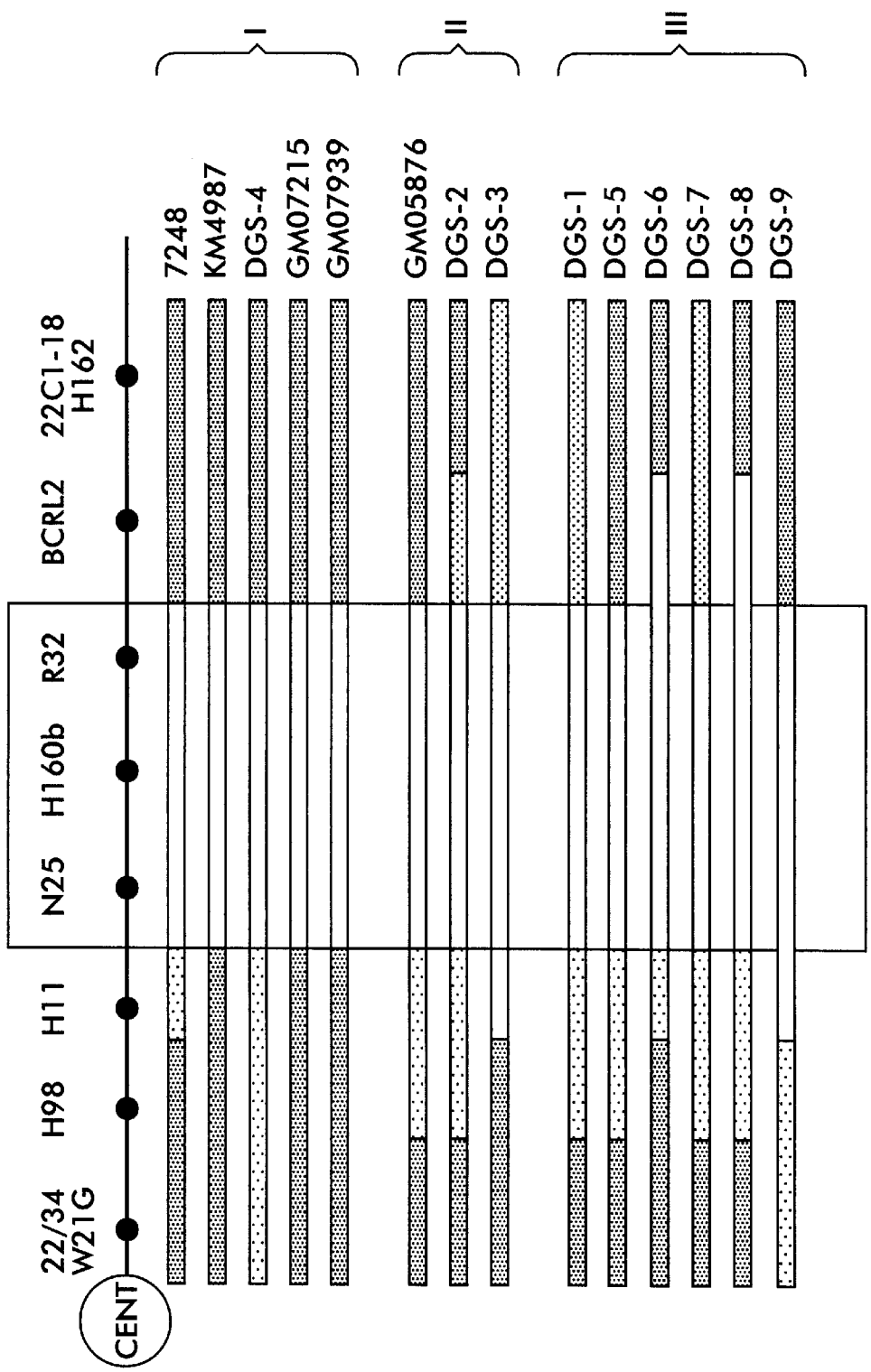
FIG. 1 is a graphic representation of RFLP and dosage studies of fourteen DGS probands, grouped according to cytogenetic findings. "I" represents del(22)(q11.21q11.23), "II" represents possible deletion of 22q11; "III" represents normal karyotype. Probes are ordered from centromere (cent) to telomere (right). The bars represent results of hybridization studies; fully shaded bars represent the presence of two copies of the locus; hatched bars represent uninformative or non-polymorphic loci for which dosage has not been performed to determine copy number; open bars represent deletions (singe allele). The minimal region of overlap is indicated by the box and includes probes N25, pH160b and pR32.

What is meant by the "DiGeorge Syndrome Critical Region (DGCR)" as used herein refers to the region on chromosome 22 as shown in the boxed region of FIG. 1. It is believed the region spanning from N25 to R32 is approximately 1.5 megabases. Initially, the DGCR did not appear to include the chromosome loci recognized by the probe H11 (D22S36) or the loci recognized by probe BCRL2, however the DGCR was believed to extend at least about 0.5 megabases on either side of the loci recognized by probes N25 and R32, thereby encompassing a region of approximately 2.5 Mb.

Cytogenetic and molecular studies have led to the partial characterization of the DiGeorge syndrome critical region located on chromosome 22q11. Molecular studies of the two aforementioned interstitial deletion probands demonstrated that loci D22S9 and D22S43 flank the critical region proximally. Loss of an allele at a more distal locus, BCRL2, was demonstrated in one of these probands suggesting that the distal boundary for the DGS critical region is in proximity to the BCRL2 locus (Fibison et al. (1990). In a more recent study, markers, KI-506, KI-197 and KI-716 were proposed as flanking markers. In addition, DNA microdeletions were demonstrated in two probands whose karyotype was normal upon routine cytogenic analysis at the 400 band stage of resolution (Driscoll et al., 1992).

Studies of DGS probands based upon cytogenetic evidence of a deletion within chromosome band 22q11 and normal karyotype by routine chromosomal analysis support the presence of a DGS critical region within 22q11 (Fibison, et al.(1990),*Am. J. Hum. Genet* 47(3): A178, Driscoll, et al., (1990), *Am. J. Hum. Genet* 47(3): A215, Driscoll et al., 1992). Greater understanding of DGS and the critical region associated with DiGeorge syndrome, DGCR, have led to new and better methods of diagnosis. For example, fluorescence in situ hybridization utilizing cosmid clones containing probes such as N25, pH160 and R32, which are derived from the DGS critical region can be used to diagnose DGS and the related syndromes of Velocardiofacial syndrome, CHARGE association, conotruncal cardiac defect, and cleft palate. Table 7 sets out probes referred to herein as well as the loci to which they correspond. In some cases, reference to loci may be accompanied by a corresponding parenthesized reference to a probe directed to said loci.

TABLE 7

| D#/Lab name | Insert (kB) | Vector | Location |
|---|---|---|---|
| D22S75/N25 | 20.0 | NotI/EMBL4N | 22q11 |
| D22S259/pR32 | 7.0 | RI/SK+ | 22q11 |
| D22S66/pH160b | 3.0 | Hd3/pUC18 | 22q11 |
| D22S57/pH98 | 0.7 | Hd3/pUC18 | 2 2 q 1 1 |
| D22S36/pH11 | 1.0 | Hd3/pUC18 | 22q11 |
| D22S68/pH162 | 5.0 | Hd3/pUC18 | 22q11 |

Two loci have been identified, D22S75 (N25) and D22S259 (pR32), that are deleted in fourteen of fourteen DGS probands, eight with either cytogenetically visible deletions or possible deletions within 22q11 and six cytogenetically normal probands. In addition, deletions of D22S66 (pH160b) have been demonstrated in eight of eight probands studied including three with normal karyotypes. It is believed that this locus is deleted in the remaining six probands based on its location between D22S75 and D22S259, both of which are consistently deleted in these fourteen DGS probands. De novo deletion of loci in the DGS critical region has also been demonstrated by RFLP analysis. The presence of a DGS critical deleted region and a minimal region of overlap have been established. Based on preliminary pulsed field gel electrophoresis data the size of the region is estimated to be approximately 0.75 megabase.

Although hemizygous DGS probands at proximal locus D22S36 (pH11) have been identified using RFLP analysis, the demonstration of heterozygous probands seemed to excludE this locus from the minimal critical region. However, as disclosed below, further studies suggest its inclusion. Dosage studies of DGS probands demonstrate that the more distal BCRL2 locus is not consistently deleted in DGS. Therefore, it has been concluded that the minimal critical region extends from, and includes, D22S36, proximally, to BCRL2, distally. The breakpoint of the ADU/VDU translocation falls between pH11 and N25.

The origin of the de novo deletions was established by RFLP analysis of five informative families. Four of five probands failed to inherit a maternal allele; one proband did not inherit a paternal allele. Based on this data and reports of both maternally and paternally inherited translocations in DGS patients there does not appear to be a consistent parent of origin or imprinting effect (de la Chapelle et al., (1981), *Hum. Genet.* 57: 253–256; Kelley et al., (1982), *J. Pediatr.* 101: 197–200; Greenberg et al., (1984), *Human Genet.*, 65: 317–319; Augusseau et al., (1986), *Human Genet.* 74:206; Bowen et al., (1986), *Clin. Genet.* 29: 174–177; Pivnick et al., (1990), *Am. J. Med. Genet.* 37: 92–96; El-Fouly et al., (1990), *Am. J. Med. Genet.* 38: 569–578). This is in contrast to what has been observed in other microdeletion syndromes such as Prader-Willi and Angelman syndromes where paternal and maternal deletions, respectively, are the rule (Knoll et al., (1989), *Am. J. Med. Genet.* 32: 285–290).

There are several features of chromosome 22 which might account for the various patterns of inheritance observed in association with DGS. These include its high recombination rate, acrocentric morphology and frequent involvement in translocations. There is evidence for a high rate of recombination in the proximal region of 22q11 from meiotic mapping studies (Fibison et al., (1990), *Am. J. Hum. Genet.* 47(3):A178). This could produce de novo 22q11 interstitial deletions, accounting for the sporadic cases of DGS. Dosage analysis with pR32 (D22S259) demonstrated loss of an allele in a DGS-affected offspring (DGS-7) of D22S259 heterozygous parents. These results are consistent with a de novo deletion in the proband which presumably arose during meiosis, perhaps as a result of recombination. Gonadal mosaicism, although rare, could give rise to affected siblings.

All fourteen DGS cases studied have either cytogenetically visible deletions utilizing high resolution banding techniques or submicroscopic deletions detected by molecular analysis with probes from 22q11. This strongly supports a systematic approach for the detection of deletions in DGS which combines both high resolution cytogenetic analysis and molecular analysis with probes for the critical region. Chromosomal analysis may detect translocations or cytogenetic abnormalities of chromosomes other than 22 however, results suggest that molecular studies may actually be more sensitive than high resolution cytogenetic analysis for the detection of small interstitial deletions. These deletions are quite difficult to visualize in this small, primarily euchromatic chromosome. Hence, chromosome 22 specific cosmids for the loci identified in the critical region should prove to be useful reagents for the rapid detection of microdeletions in the diagnosis of DGS.

Smaller interstitial deletions are believed to produce a less severe phenotype, for example the phenotype associated with the so-called partial DiGeorge syndrome. Reproduction for less severely affected patients might not be compromised and DGS associated with a deletion could appear to segregate, at least in some cases, as an autosomal dominant disorder. In support of this hypothesis deletions of loci within the DGS critical region have been demonstrated in a mother and child with Velocardiofacial syndrome, an autosomal dominant disorder often associated with features of DGS (unpublished results; Shprintzen et al.et, (1985), *Am. J. Human Genet.* 37: A77; Goldberg et al., (1985), *Am. J. Hum. Genet.* 37: A54; Stevens et al., (1990), *Pediatrics* 85: 526–530). Identified deletions in this region may account for the overlapping phenotypic features between DGS and Velocardiofacial syndrome. Fourteen of 15 VCF patients studies have either cytogenetically visible interstitial deletions of 22q11.2 or submicroscopic deletions of DNA within the DGCR. These 14 patients have deletions of both the most proximal marker (N25) and distal marker (pR32) in the DGCR. This would account for the overlapping phenotypic features observed in VCF and DGS. At this time, molecular differences have not been identified to explain the phenotypic variability among VCF patients or between these two groups of patients. Preliminary studies of the DGCR suggest that this region is large (greater than 750 kb) and contains several genes (Driscoll et al. (1992), *Am. J. Hum. Genet.* 50: 924–933 (1992a). It is believed that in some cases deletions or mutations of different loci within 22q11 may correlate with the presence of individual clinical features such as cleft palate, cardiac defect and thymic hypoplasia or aplasia. However, phenotypic differences between patients or within families may result from differences in genetic background as well as intra-uterine environment.

This is the first study to demonstrate failure to inherit a 22q11 allele in a VCF proband by RFLP analysis of both the affected parent and child (VCF-4/VCF-5 and VCF-10/VCF-11). In these families, hemizygosity at D22S75 and D22S259 was also confirmed in the affected parents and their offspring by dosage analysis. A fluorescence in situ hybridization assay using N-25 YAC and cosmid probes confirmed the presence of a single allele in VCF-10 and VCF-11.

The autosomal dominant inheritance pattern observed in the VCF families in this study is the result of inheritance of a deletion-bearing chromosome rather than a mutation in an autosomal dominantly inherited gene. The results of this study suggest that in most cases VCF is a segmentally aneusomic disorder. However, one of the probands studied (VCF-6) is not deleted at either D22S75 (N25) or D22S259 (pR32). Several of his clinical features are atypical for VCF. Follow-up concluded that the patient was incorrectly diagnosed with VCF.

Seventeen patients with the CHARGE association have also been studied. Fourteen have been studied by dosage with N25 and a deletion has been detected in one patient. This individual is not deleted for R32. All seventeen patients have been studied by dosage with R32 and only a single patient demonstrated a deletion.

In addition, nine patients with isolated conotruncal cardiac malformations have been studied. Of these patients, four are deleted for N25. Three of these patients are also deleted for R32. These data suggest deletion of overlapping segments of 22q11.2 as genetic etiology for these disorders.

It was hypothesized that balanced translocations between the proximal long arms of acrocentric chromosomes might account for some cases of DGS. During meiosis, all five pairs of acrocentric chromosomes coalesce around the nucleolus. It has been suggested that Robertsonian translocations occur at this time. Balanced translocations between the proximal long arms of the acrocentric chromosomes might also occur at this stage of meiosis. Malsegregation of a translocation with breakpoints in 22q11 and the q11 region of any of the other acrocentric chromosome could produce 22pter->q11 monosomy and trisomy for pter–>q11 of the other involved acrocentric which might remain undetected upon standard cytogenetic analysis. Malsegregation of such cryptic balanced translocations could produce DGS affected siblings in families, whereas trisomy for the other involved acrocentric autosome could explain the phenotypic variability seen between DGS patients.

It has been observed that, amongst constitutional chromosomal abnormalities, a greater than expected number of visible translocations involve chromosomal band 22q11 (Yu et al., 1978). These findings support schemes presented for generating familial DGS cases. Investigation of these DGS-generating mechanisms was facilitated by fluorescence in situ hybridization analysis of DGS patients and their parents using centromere-specific probes for each of the acrocentric chromosomes, together with hybridization probes to the DGS critical region provided by the present invention.

As described above, DGS was associated with visible chromosomal abnormalities (primarily deletions of 22pter-q11), microdeletions of 22q11, exposure to teratogens and maternal diabetes. In the vast majority of cases (>85%), DGS results from a microdeletion of chromosome 22, del (22) (q11.21q11.23). (Driscoll et al., 1992). As described hereinafter, DGS has now been associated with a balanced translocation—the ADU t(2;22) (q14;q11.21)—which is placed in the critical region.

In 1986 Augusseau et al., *Hum. Genet.* 74:206, 1986. described a patient (ADU) with "partial" DGS. She had telecanthus, microretrognathia, severe aortic coarctation with hypoplastic left aortic arch, decreased E rosettes, and mild neonatal hypocalcaemia. Cytogenetic analysis of this individual revealed an apparently balanced translocation between chromosomes 2 and 22, resulting in a karyotype of 46, XX,t (2;22) (q14;q11), the resultant chromosomes are hereinafter referred to as der(2) and der(22). The translocation breakpoint is within the 2.5 Mb DGCR. The same translocation was present in her mother (VDU). In the original paper, VDU was reported to have no features of DGS. However, subsequent publications cite VDU as mildly affected with hypernasal speech, micrognathia, and inverted T4/T8 ratio, features seen in VCFS and DGS. (Demczuk et al., *Hum. Molec. Genet.,* 4:551–558, 1995.) The DGS phenotype in ADU, the VCFS phenotype in VDU and a balanced translocation of chromosome 22 in both individuals renders this translocation a primary target of positional cloning approaches to assist in identification of the gene(s) responsible for DGS and VCFS. The ADU and VDU rearrangements are identical at a molecular level. Thus, the most likely explanation for the more severe phenotype in the proband is that the effect of the disrupted gene at the breakpoint is modified by other factors. Such phenotypic variability has been observed previously with DGS, and may be attributed to a variety of factors including the in utero environment, teratogens, and maternal diabetes.

That the ADU/VDU translocation is the only known balanced translocation associated with DGS suggests that the ADU/VDU breakpoint interrupts a locus or loci critical to DGS. The positioning of the breakpoint within the minimal DGCR supports this conclusion.

The cloning of this translocation breakpoint, the identification of a gene disrupted by the rearrangement, and the analysis of other transcripts in its vicinity are reported below. The transcripts were identified by direct screening of cDNA libraries as well as exon amplification, cDNA selection, and genomic sequence analysis using a computer-based approach and the program GRAIL prediction. Our analyses suggest that there are at least two transcripts on opposite strands in the region of the t(2;22) breakpoint. Through extensive sequence analysis, we have ascertained that the breakpoint disrupts a predicted ORF (exon rnex40) of one of these genes, introducing a stop codon approximately 20 amino acids downstream of the breakpoint, and deletes eleven nucleotides at the translocation junction, making this gene a DGS/VCFS candidate locus. The precise location of the translocation junction depends upon which partner lost the GTG or GG. The novel gene disrupted by the t(2;22) identifies a low abundance message, further implicating this locus as a DGS candidate gene. The predicted protein shows weak homology to the mouse and rat androgen receptor locus and contains a leucine zipper motif, suggesting that the DGS candidate gene may be a DNA binding protein. Following the recently proposed nomenclature (Desmaze et al., *Am. J. Hum. Genet.,* 53:1239–1249, 1993), this ADU/VDU candidate locus could be called DGCR3.

Another partial transcript, nex2.2-nex3, may link to ac2b1 which would represent a second gene, i.e., DGCR4, disrupted by the breakpoint. Both loci are deleted in all deletion positive patients studied (22/22) and fall within the minimal deleted region whose distal boundary is defined by the t(X;22) breakpoint.

Additional experiments will determine whether one or both genes are important in the etiology of DGS/VCFS. However, disruption of a gene in 22q11.2 by the t(2;22) breakpoint and haploinsufficiency of this locus in 22q11.2 deleted DGS patients make it a strong candidate for the major features associated with this disorder.

Several expressed sequences have been previously described as mapping into the DGCR. Two novel cDNAs in the DGCR have been isolated by screening cDNA libraries with NotI linking clones N41 and N25 (Emanuel et al., *The Phenotypic Mapping of Down Syndrome and Other Aneuploid Conditions,* edited by Epstein, C., Wiley-Liss, Inc., N.Y., pp207–224, 1993). A zinc finger gene, ZNF74, was identified by screening chromosome 22 human libraries (Aubry et al., *Hum. Molec. Genet.,* 2:1583–1587, 1993) and shown to be deleted in 23/24 DGS patients. T1O was identified from a mouse embryo library and shown to be expressed during early mouse embryogenesis as well as in human fetal tissue. The T10 cDNA lies within the commonly deleted region but outside the minimal critical region (Halford et al., *Hum. Molec. Genet.,* 2:1577–1582, 1993b) as do COMT (Grossman et al., *Genomics,* 12:822–825, 1992) and GPIBβ (Budarf et al., *Hum. Mol Genet., in press,* 1995). The gene TUPLE1 (Halford et al., *Hum. Molec. Genet.,* 12:2099–2107, 1993), has been described as a candidate for the central features of the syndrome. Although it has been shown to be deleted in the majority of patients with known 22q11 deletions, it does not appear to be mutated or rearranged in non-deleted patients with DGS. Recently, Demczuk et al., *Hum. Molec. Genet.,* 4:551–558, 1995, described a gene, DGCR2, which maps 10 kb telomeric to the ADU/VDU breakpoint. By sequence analysis, DGCR2 appears to be homologous to the gene designated LAN below. LAN is not believed to be the critical DGS locus in ADU/VDU because of its position and direction of transcript with respect to the ADU/VDU breakpoint. All of these loci map distal to the t(2;22) and, are not disrupted by the 2;22 translocation.

Additional support that either of the genes identified herein is of significance in the etiology of DGS will lie in determining whether all deleted patients are hemizygous for these loci and whether mutations in these genes are detectable in non-deleted patients with features of DGS. Until such evidence is available, there will still remain the possibility that the translocation separates a locus control region from its target gene or produces a position effect.

Molecular or molecular-cytogenetic studies with probes from the DGCR are clearly the most sensitive means of detecting deletions, translocations, and mutations involving 22q11. Cytogenetic analysis utilizing high-resolution banding techniques will only detect about 20% of the deletions in this region (VCF-1, VCF-9, VCF-14). Thus, it is believed that cytogenetic analysis is of limited usefulness. Like the detection of deletions in DGS patients, these data support a molecular approach for analysis of patients with VCF. RFLP and DNA dosage studies utilizing probes from the DGCR are useful however, it is believed believe that FISH will be a more rapid and cost efficient method for the detection of deletions.

Probes and methods of producing probes directed to the DGCR as well as methods of detecting genetic deletions, translocations, and mutations associated with DGS, Velo-cardiofacial syndrome, CHARGE association, conotruncal cardiac defect and cleft palate using probes are provided by the present invention. Kits useful for detection of these genetic deletions and mutations are also provided. The term "mutation" as used herein is meant to refer to a change in the structure of a gene, such as a nucleic acid sequence which varies in as little as one base from the naturally occurring nucleic acid sequence of the gene.

Accordingly, the invention provides methods of detecting deletions, translocations, and mutations associated with a condition selected from the group consisting of DiGeorge syndrome, Velocardiofacial syndrome, CHARGE association, conotruncal cardiac defects and cleft palate in a human patient. It is believed that Velocardiofacial syndrome, CHARGE association, conotruncal cardiac defects and cleft palate in a human patient are caused by deletions or mutations of a locus or loci in the DiGeorge Syndrome Critical Region. Carey, J. C., *J. Pediatrics,* 96:955–956 (1980);

Lammer et al., *Am. J. Med. Genet.*, 2 (suppl.), 113–127 (1986). The methods comprise the step of providing a DNA containing test sample from said human patient. Appropriate test samples such as blood are well known to those in the art. Finally, there is identification of whether there are less than two functional copies of the DiGeorge syndrome critical region loci present in the test sample. Identification can be accomplished in a number of ways such as through the polymerase chain reaction (PCR) or hybridization such as in situ hybridization or restriction fragment length polymorphism (RFLP). PCR is described in U.S. Pat. No. 4,386,202 issued to Mullis which patent is incorporated by reference as if fully set forth herein.

In situ hybridization can be accomplished by contacting a detectably labeled nucleic acid probe, said probe being substantially complementary to unique sequences in the DiGeorge syndrome critical region, with said test sample under hybridizing conditions; and detecting hybridization of said detectably labeled probe with DNA of chromosome 22.

Hybridization of detectably labeled probes and the DGCR occurs under hybridization conditions which will be apparent to those skilled in the art and described in the Examples set forth herein. In one embodiment of the present invention hybridization was performed at 42° C. with 50% formamide, 0.1×SSC, 0.1% SDS, 3×SSC, 1% SDS, 5% dextran sulfate, denatured herring sperm DNA (100 μg/ml). In an alternative embodiment of the present invention hybridization may be performed at 65° C. with 1% SDS, 1M NaCl and 10% dextran sulfate.

Detectably labeled probes of the present invention which are substantially complementary to said DGCR will hybridize to said DGCR under hybridizing conditions. The term "substantially complementary" is used herein to describe the commonly understood interaction of complementary base pairing. Imperfect pairing, whether due to deletions or imperfect base matching (i.e. mutation), is envisioned by the present invention when said pairing results in hybridization.

The identification of less than two functional copies of the DiGeorge syndrome critical region loci is indicative of a likelihood that the tested person has a genetic deletion or mutation associated with at least one of DiGeorge syndrome, Velocardiofacial syndrome, CHARGE association, conotruncal cardiac defects and cleft palate.

In another aspect of this invention there is provided a method of preparing diagnostic probes useful for the detection of deletions and mutations associated with a condition selected from the group consisting of DiGeorge Syndrome, Velocardiofacial syndrome, CHARGE association, conotruncal cardiac defects and cleft palate. Primers are prepared which are effective to amplify a region of chromosome 22q11 shown to be unique sequences in the DiGeorge syndrome critical region. DNA is synthesized which is substantially complementary to a region of normal human genomic DNA or cDNA by PCR amplification using pairs of said primers; and a DiGeorge syndrome critical region probe is then isolated from libraries containing human chromosome 22 using the substantially complementary DNA.

Conveniently, primers are selected from the group consisting of 5'ACACTGGTCCACAGTGCCAG3' (SEQ ID NO:1) and 5'TGTGAGGGCTTGCTCTGAGC3' (SEQ ID NO: 2); 5'TGGTACCGCTGCTCAGAGGGC3' (SEQ ID NO:3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6) ADU1F, 5'CACCGTGCTCTGCTAAATGA3' (SEQ ID NO: 7); and ADU1R, 5'GCTCTGAGT-CAAAAGGGTGC3' (SEQ ID NO:8); der(2)R, 5'CTT-TAATGAGCCCACCTCCA3' (SEQ ID NO:16); and der(22)F, 5'GGTGGCTTTTCCAGGTGTTA3' (SEQ ID NO:17).

Alternatively, probes useful for the detection of genetic deletions, translocations, and mutations associated with a condition selected from the group consisting of DiGeorge Syndrome, Velocardiofacial syndrome, CHARGE association, conotruncal cardiac defects and cleft palate are prepared according to the following steps: PCR amplifying a region of a normal human genomic DNA using the a pair of PCR primers selected from the group consisting of 5'ACACTGGTCCACAGTGCCAG3' (SEQ ID NO:1) and 5'TGTGAGGGCTTGCTCTGAGC3' (SEQ ID NO:2); 5'TGGTACCGCTGCTCAGAGGGC3' (SEQ ID NO;3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6); and probing a library containing human chromosome 22 sequences with said amplified DNA to isolate a fragment or clone which hybridizes with said amplified DNA; or PCR amplifying a region of der(2) or der(22) using primers selected from the group consisting of der(2)R, 5'CTTTAAT-GAGCCCACCTCCA3' (SEQ ID NO:16); and der(22)F, 5'GGTGGCTTTTCCAGGTGTTA3' (SEQ ID NO:17); and a library containing der(2) and der(22) sequences with said amplified DNA to isolate a fragment or clone which hybridizes with said amplified DNA.

In another alternative, a diagnostic probe useful for the detection of genetic deletions, translocations, and mutations associated with a condition selected from the group consisting of DiGeorge syndrome, Velocardiofacial syndrome, CHARGE association, conotruncal cardiac defects, and cleft palate is prepared by PCR amplifying a clone from a library containing chromosome 22 to identify clones containing the probe.

Diagnostic kits for the detection of genetic deletions, translocations, and mutations associated with a condition selected from the group consisting of DiGeorge syndrome, Velocardiofacial syndrome, CHARGE association, conotruncal cardiac defects and cleft palate comprising a diagnostic probe selected from the group consisting of probes and primers as prepared and described herein.

It was recently reported that anomalies which best differentiated schizophrenics from controls are frequently identified in patients with VCFS (Pulver et al., *Am. J. Med. Gen. (Neuropsychiatric Genetics)*, 54:36–43, 1994, incorporated herein by reference). A potential linkage of schizophrenia for 22q12-q13.1 was reported. The close proximity to the deleted region in VCFS was noted and it was concluded that the data may be interpreted as suggesting that some DNA deletion or re-arrangement in the area is involved in both disorders. Accordingly, it is contemplated that the methods, probes, and kits according to the invention may also be utilized in the detection of deletions, translocations, and mutations associated with schizophrenia.

The following examples are illustrative and are not meant to be limiting of the present invention.

EXAMPLE 1

Preparation of Cell Lines

Three cell lines (GM07215, GM07939, GM05876) were obtained from the Coriell Cell Repository (Coriell Institute for Medical Research, Camden, N.J.). Two additional cell lines have been previously described; 7248 (Greenberg et al., (1988), *Am. J. Hum. Genet.* 43: 605–611) and KM4987

(Mascarello et al., (1989), *Am. J. Med. Genet.* 32: 112–114). Patients were obtained from Children's Hospital of Pennsylvania, Philadelphia, Pa. and referring physicians. Blood or skin was obtained to establish lymphoblastoid or fibroblast cell lines. Lymphoblastoid cell lines were established on the parents whenever possible. The analysis includes a total of five DGS families and three VCF families.

EXAMPLE 2
Preparation of Probes

The probes utilized in this study include anonymous markers pH98 (D22S57), pH11 (D22S36), pR32 (D22S259), pH160b (D22S66), pH162 (D22S68) isolated from flow sorted chromosome 22 libraries (Budarf et al., (1991), *Genomics* 3: 168–171). Clone N25 (D22S75) isolated from a NotI linking library (McDermid et al., (1989), *Genomics* 5: 1–8); probe p22/34 (D22S9), isolated from a chromosome 22 enriched library and localized by in situ hybridization to 22q11 (McDermid et al., (1986), *Science* 232:646–648); and probe W21G (D22S24), derived from a flow-sorted chromosome 22 library (Rouleau et al.,(1989), *Genomics* 4:1–6) were also used. The probe used for the BCR-related genes is a 160 bp cDNA HindIII/EcoRI fragment from the 3' end of the BCR gene (Budarf et al., (1988), *Genomics* 10:996–1002; Croce et al., (1987) *Proc. Natl. Acad. Sci.* 84: 7174–7178). Probes, βIVS2 and CRI-R365 (D11S129) were used as internal control probes for the dosage studies. Both probes map to chromosome 11 and are not affected by DGS. $\beta IVS_2$ is a 920 bp unique fragment derived from the second intervening sequence of the β-globin gene. CRI-R365 is a unique 2 kb HindIII fragment (Donis-Keller et al.,(1987), *Cell* 51: 319–337).

EXAMPLE 3
Clinical and Cytogenetic Studies of DGS Patients

Clinical information was obtained either from the referring physicians or from the literature for published cases. High resolution cytogenetic analysis at the 800–850 band stage was performed using standard techniques.

Cytogenetic analysis of the three cell lines obtained from the CCR (Coriell Cell Repository) were initially reported as normal at the 400–450 band stage of resolution. Repeat analysis utilizing high resolution banding techniques demonstrated visible interstitial deletions of 22q11 in GM07215 and GM07939; GM05876 has a possible deletion. Patients 7248, KM4987 and DGS-4 have del 22(q11.21-q11.23). Patients DGS-2 and DGS-3 have possible cytogenetic deletions within 22q11. Patients DGS-1, DGS-5, DGS-6, DGS-7, DGS-8 and DGS-9 have normal karyotypes utilizing high resolution banding techniques. Table 1 summarizes the cytogenetic and clinical findings in the patients.

EXAMPLE 4
DNA Studies of DGS Patients.

DNA was extracted from the DGS and parental cell lines by routine methods and was digested with restriction enzymes as recommended by the manufacturer (New England BioLabs). Digested DNA was separated by agarose gel electrophoresis and transferred to either Immobilon (Millipore) or Gene Screen Plus (Dupont) using the method of Southern (Southern, (1975), *J. Mol. Biol.* 98: 503–517). DNA probes were digested with the appropriate restriction enzymes and purified in low melt agarose by gel electrophoresis. DNA probes were labelled with $[\alpha-^{32}P]dCTP$ using the random primer method (Feinberg and Vogelstein, (1984), *Anal. Biochem.* 137: 266–267). Labelled probes N25, pR32 and p160b were preannealed with sonicated placental DNA (Litt and White, (1985), *Proc. Natl. Acad. Sci. U.S.A.* 82: 6206–6210). Hybridization was at 42° C. with 50% formamide, 0.1×SSC, 0.1% SDS, 3×SSC, 1% SDS, 5% dextran sulfate, denatured herring sperm DNA (100 μg/ml) or at 65° C. with 1% SDS, 1M NaCl and 10% dextran sulfate. Filters were washed twice with 0.2×SSC, 0.1% SDS at 65° C. and exposed to Kodak XAR-5 film at −70° C. for varying lengths of time.

DNA obtained from cell lines of patients with DGS and their parents was studied by RFLP analysis as described above. Deletions were detected by demonstration of failure to inherit a parental allele. If parental DNA was unavailable, DGS patient cell lines were analyzed for the presence of two alternative alleles. Families who were uninformative using RFLPs and probands demonstrating a single allele at a test locus were subsequently studied with dosage analysis. Probes pH11 (D22S36), N25 (D22S75) and pR32 (D22S259) detected deletions in the five DGS patients for whom parental DNA was available. Deletions were detected in two patients with normal karyotypes, two with visible interstitial deletions and a fifth proband whose cytogenetic study was inconclusive for a deletion.

Probe pR32 (D22S259) was informative in three of five families. This probe detects a 10.1 kb and 9.4 kb allele. Probe pR32 was informative in three families, those of probands 7248, DGS-4 and DGS-5. The father is heterozygous in each family. The mothers of 7248 and cytogenetically normal DGS-5 are homozygous for the 9.4 kb allele. The probands in these two families have a single band, a 10.1 kb allele, inherited from the father. Thus, the child in each of these two families failed to inherit a maternal allele, a 9.4 kb band. The mother of DGS-4 is homozygous for the 10.1 kb allele. The proband has a single 9.4 kb allele shared by the father. This is consistent with a deletion of a maternal allele in these three families. Two of our five DGS families were uninformative at this locus. Nine additional individual DGS probands tested demonstrated a single RFLP allele, consistent with either hemizygosity or dizygosity at this locus. Dosage studies were performed to determine if one or two copies of locus D22S259 were present in these eleven uninformative probands.

Probe N25 (D22S75) was informative in one of five families. One proband with a visible interstitial deletion of 22q11, DGS-4, demonstrated loss of a maternal allele at locus D22S75 (N25) (FIG. 2). The probe N25 detects a TaqI polymorphism, producing alleles of 3.3 or 2.3 and 0.96 kb and a 1.6 kb constant band (Fibison et al., submitted). The father of DGS-4 is homozygous for the 3.3 kb allele; the mother is homozygous for the 2.3 and 0.96 kb allele. Proband DGS-4 has a single band at 3.3 kb, inherited from his father. This is consistent with the loss of the maternal allele at locus D22S259 (pR32) described above for this family. Southern blot analyses of nine individual DGS patients revealed a single allele, again, requiring dosage analysis to determine zygosity.

Two of the five DGS families were informative at locus D22S36 (pH11). RFLP analysis with probe pH11 demonstrated loss of a parental allele in proband DGS-3, who has a possible cytogenetic deletion, and DGS-9, who has a normal karyotype (FIG. 3). Probe pH11 detects a MspI polymorphism which produces two alleles, 3.3 and 1.6 kb, and two constant bands, 3.7 and 2.3 kb. The parents of DGS-3 are homozygous for different alleles. DGS-3 has a 3.3 kb allele shared by his father and he failed to inherit a maternal allele (1.6 kb). The father of the proband DGS-9 is homozygous for the 1.6 kb allele; the mother is heterozygous at this locus. Proband DGS-9 demonstrated a single 3.3 kb allele shared with her mother. She did not inherit a paternal allele. Although nine probands demonstrated single alleles consistent with either hemizygosity or dizygosity at this locus, three probands (KM4987, GM07215, GM07939) were heterozygous. The presence of heterozygous DGS probands excludes locus D22S36 from the minimal critical region.

Table 2 summarizes the results of RFLP analysis of DGS cell lines utilizing eight polymorphic probes previously localized to 22q11. Hemizygous patients are those who failed to inherit a parental allele by RFLP analysis. Eight loci were examined for RFLP status in 5 families. Of the 40 loci tested in the five DGS probands, six deleted loci were ascertained as failure to inherit a parental allele. All deletions were observed at three of the eight loci, D22S36 (pH11), D22S75 (N25) and D22S259 (pR32). Deletions were detected in all five probands using RFLP-based family studies. In addition, nine individual DGS probands were examined for the presence of heterozygosity at these three loci. All of these probands demonstrated a single allele at D22S75 (N25) and D22S259 (pR32) requiring dosage studies. Three probands were heterozygous at D22S36 (pH11), placing D22S36 outside the DGS critical region. RFLP analysis with proximal loci D22S24 (W21G), D22S9 (p22/34) and D22S57 (pH98) and the more distal loci D22S10 (22C1-18) and D22S68 (pH162) failed to detect deletions in the five families studied and thirty to forty percent of the probands tested were heterozygous at these loci. Therefore, based on RFLP analysis proximal loci D22S24, D22S9, D22S57, and D22S36, and distal loci, D22S10 and D22S68 must lie outside the DGS minimal critical region.

EXAMPLE 5
Dosage Analysis of DGS Patients

For cell lines demonstrating a single allele at loci D22S75 (N25) and D22S259 (pR32), Southern blots of HindIII-digested DNA were analyzed by the AMBIS Radioanalytic Imaging System to determine the number of alleles present. Probe N25 detects a 2.6 kb HindIII fragment. The internal control probe, βIVS2 recognizes a distinct 7.8 kb fragment. Southern blot analysis can be used, the intensity of the equivalent hybridization signals for N25 in the two DGS probands is less than that observed in the control when compared with the hybridization signals for βIVS2. Approximately one-half the expected ratio of the counts obtained with N25 to βIVS2 was observed in thirteen of thirteen probands (Table 3). These results are consistent with loss of an allele at locus D22S75 (N25).

Probe pR32 (D22S259) detects an approximately 23 kb Hind III fragment. The ratio of the signal obtained from pR32 to βIVS2 was less than one-half, consistent with the presence of a single allele in the thirteen DGS probands tested (Table 4). Three probands including two of these thirteen (DGS-4, DGS-5) demonstrated loss of a parental allele by RFLP analysis.

Dosage studies were performed with pH160b (D22S66), a nonpolymorphic probe, which has been sublocalized to 22q11 by hybridization to a somatic cell hybrid mapping panel (Budarf et al. ,(1991), *Genomics* 10: 996–1002). This locus appears to lie between D22S75 (N25) and D22S259 (pR32) (M. Budarf, unpublished results). Probe HI60b recognizes a 2.3 kb HindIII fragment. Loss of an allele was demonstrated in 8 of 8 patients studied (Table 5).

A probe derived from the 3' end of the BCR gene detects four loci: BCR, BCRL2, BCRL3, and BCRL4. These loci map in distinct and separate regions of 22q11 with BCRL2 as the most proximal of these four loci. A HindIII digest produces 23, 19.5, 13 and 9 kb fragments which recognize BCR, BCRL3, BCRL2 and BCRL4, respectively (Croce et al., (1987), *Proc. Natl. Acad. Science, U.S.A.* 84: 7174–7178). Either probe βIVS2 or CRI-R365 which recognizes a 2 kb fragment was used as a control probe. The ratio of the counts obtained from BCRL2 to the control probe was consistent with a deletion of BCRL2 in two DGS cell lines. However, the ratios between the test probe and control probe were similar in seven cell lines (Table 6). Therefore, BCRL2 lies outside the minimal critical region for DGS.

EXAMPLE 6
Clinical and Cytogenetic Studies of VCF Patients

Fifteen patients including two affected mothers and their affected daughters were referred with the diagnosis of VCF.

Cytogenetic analysis of metaphase chromosomes was performed at the 800–850 band level of resolution using standard techniques. Table 8 summarizes the clinical features of the VCF patient studies.

TABLE 8

Summary of Clinical Findings of VCF Patients

| Patient | Palatal Abnormality | Cardiac Defect | Learning Disability | Typical Facies | Other |
|---|---|---|---|---|---|
| VCF-1 | + | − | + | + | |
| VCF-2 | −[c] | − | + | + | |
| VCF-3 | + | − | + | + | parent of 3 affected offspring[d] |
| VCF-4 | + | PDA | + | + | growth retardation, hypothyroidism, inguinal hernia, retinal vessel tuortuosity, 2–3 syndactyly |
| VCF-5[a] | + | VSD | + | + | retinal vessel tortuosity, exotropia, 2–3 syndactyly |
| VCF-6 | + | perimembranous VSD | + | + | growth retardation, hypospadias |
| VCF-7 | + | VSD, rt. aortic arch | + | + | |
| VCF-8 | + | Rt. aortic arch | + | + | |
| VCF-9 | + | TOF, rt. aortic arch | + | + | microcephaly, brachydactyly |
| VCF-10[b] | + | − | + | + | |

TABLE 8-continued

Summary of Clinical Findings of VCF Patients

| Patient | Palatal Abnormality | Cardiac Defect | Learning Disability | Typical Facies | Other |
|---|---|---|---|---|---|
| VCF-11 | + | − | + | + | |
| VCF-12 | + | − | + | + | retinal vessel tortuosity |
| VCF-13 | + | VSD coarctation of aorta | + | + | |
| VCF-14 | + | VSD coarctation of aorta | + | + | laryngeal web, psychiatric illness |
| VCF-15 | + | − | + | + | growth retardation, hypocalcemia |

(+) indicates presence of clinical feature;
(−) indicates absence of clinical feature.
VSD = ventricular septal defect;
TOF = tetralogy of Fallot;
[a]Mother of VCF-4;
[b]Mother of VCF-11;
[c]hypernsal speech;
[d]offspring have not been studied.

All of the patients have the characteristic facial features described by Shprintzen et al. (1978), *Cleft Palate J.* 15: 56 and Shprintzen, et al. (1981), *Pediatr.* 67: 167–172 and learning disabilities. However, in addition to a cleft palate, perimembranous VSD and hypospadias, patient VCF-6 appears to have a more severe degree of developmental delay and growth retardation than previously reported in VCF. Fourteen patients have palatal abnormalities including cleft palate and velo-pharyngeal insufficiency. The remaining patient (VCF-2) has hypernasal speech. Cardiac defects were found in 8 of 15 patients.

Three of 15 patients (VCF-1, VCF-9, VCF-14) have interstitial deletions of 22q11 [del(22) (q11.21q11.23)]. The remaining 12 patients have normal karyotypes using high-resolution banding techniques (800–850 band level of resolution).

EXAMPLE 7

DNA Studies of VCF Patients

DNA obtained from cell lines of 15 patients with VCF and their parents, when available, was studies by RFLP analysis with probes N25 (D22S75) and pR32 (D22S259). Deletions were detected in three patients with normal karyotypes by demonstration of failure to inherit a parental allele either at locus D22S259 or D22S75. An autoradiogram of two Southern blots of genomic DNA digested with TaqI and probed with pR32 (D22S259) shows that the probe detects either a 10.1 or a 9.4 kb allele. The unaffected parents are homozygous for alternate alleles. The proband (VCF-8) has a single allele shared by here mother; she failed to inherit a paternal allele. In another case the mother (VCF-5) has a 10.1-kb allele while here daughter (VCF-4) has a 9.4-kb allele. Thus, VCF-4 did not inherit a maternal 10.1-kb allele. One family (VCF-10, VCF-11) was informative at locus D22S75 (N25). Proband VCF-1 and her affected mother (VCF-10) do not share the same band therefore, VCF-10 did not inherit a maternal allele. The remaining 11 probands studied demonstrated a single band at both loci D22S75 and D22S259. This is consistent with either 1 or 2 copies of the locus (hemi- or homozygosity, respectively) and required dosage analysis to determine the number of alleles present.

EXAMPLE 8

Dosage Analysis of VCF Patients

All of the VCF patients including patients shown to be deleted by RFLP analysis were analyzed for copy number at loci D22S75 (N25) and D22S259 (pR32). Southern blots of restriction enzyme digested DNA were analyzed by the AMBIS Radioanalytic Imaging System to determine the number of alleles present. The results of these quantitation experiments are summarized in Table 9.

TABLE 9

Summary of Dosage Analysis of VCF Cell Lines by Quantitative Hybridization

| Patient | N25 | Probe pR32 |
|---|---|---|
| VCF-1 | 1.00 | 1.04 |
| VCF-2 | 0.57 | 0.73 |
| VCF-3 | 1.06[b] | 0.90 |
| VCF-4 | 0.82 | 0.59[a] |
| VCF-5 | 0.41 | 0.80 |
| VCF-6 | 1.99 | 2.01 |
| VCF-7 | 1.19 | 0.98 |
| VCF-8 | 1.08[b] | 0.76[a] |
| VCF-9 | 1.12 | 1.29 |
| VCF-10 | 1.02[b] | 0.66 |
| VCF-11 | 0.82[a,b] | 0.96 |
| VCF-12 | 1.23 | 1.01 |
| VCF-13 | 1.11 | 1.08 |
| VCF-14 | 1.04 | 0.91 |
| VCF-15 | 1.09 | 1.05 |

[a]Copy number was also demonstrated by RFLP analysis.
[b]Copy number was confirmed by fluorescence in situ hybridization with N25 YAC and cosmid clones.

The values of Table 9 represent locus copy number, standardized from quantitative analysis of the hybridization signals obtained with the test probe relative to those obtained with a control probe. They were obtained by taking the mean of three independent ratios of patient to control. Values less than 1.50 are consistent with a deletion. Fourteen of 15 patients were hemizygous at both loci. A deletion at either locus was not detected in one patient (VCF-6).

Examples 9 through 17 below are directed to the translocation analyses. The following are some experimental conditions specific for these examples.

Genotyping

Genomic DNA was extracted from ADU, VDU, and normal human lymphoblastoid cell lines and somatic cell human-hamster hybrid cell line GM10888. Simple tandem repeat polymorphic markers were PCR-amplified using 100 ng genomic DNA, 125 uM each dGTP, dCTP, dTTP, DATP, 1.0 mM MgCl$_2$, 10 mM Tris, pH8.3, 50 mM KCl, 0.4 ul Taq polymerase, 18 pmol unlabelled primer, 2 pmoles γ-P$^{32}$ or γ-P$^{33}$ dATP end-labeled primer. Samples were amplified in an MJ PTC-100 thermocycler for 20–35 cycles at 94° C. for 30 seconds, 62° C. (D22S301) and 60° C. (D2S131), for 30 seconds, 72° C. for 1 minute, and 72° C. for 7 minutes. Amplification products were electrophoresed on a denaturing 6% acrylamide gel at 60% for 3–4 hrs. Gels were transferred to 3M Whatman paper, dried and exposed to autoradiographic film for 1 hr to 4 days. RFLP and Dosage analysis were performed as previously described (Driscoll et al., 1992a, supra.

STS Generation and PCR Conditions

STSs were generated from sequence derived from plasmid, phage and cosmid clones. Sequence data from an ABI automated sequencer was analyzed (Staden package, Dear et al., *Nucl. Acids Res.*, 19:3907–3911, 1991) and STSs were chosen using PRIMER (M. J. Daly, S. Lincoln and E. S. Lander, Whitehead Institute, Cambridge, Mass. 1991). PCR was performed in 20 μl reactions using approximately 80 ng genomic DNA or 2 ng of cloned DNA in standard 1×PCR buffer (BoehringerMannheim): 10 mM Tris-HCl, 1.5 mM Mg$^{++}$, 50 mM KCl, pH8.3 with 1 μM of primers (final concentration) and 0.5U Taq polymerase (Perkin Elmer Cetus or Boehringher-Mannheim). PCR conditions were: a five minute denaturation step at 95° C. followed by 30 cycles of [denaturation at 95° C. for 15 seconds, annealing at a temperature determined for each STS for 15 seconds, and extension at 72° C. for 1 minute 22 seconds] and lastly a 7 minute extension at 72° C.

The majority of PCR reactions were performed on Perkin Elmer 9600 thermal cyclers. PCR products were analyzed by gel electrophoresis using 1.5% agarose. PCR products for sequencing were purified using a StrataEluter electroelution device (Stratagene) followed by a Wizard PCR minicolumn (Promega) Primer sequences are as follows:

ADU1F, 5'CACCGTGCTCTGCTAAATGA3' (SEQ ID NO: 7);
ADU1R, 5'GCTCTGAGTCAAAAGGGTGC3' (SEQ ID NO:8);
ADU2F, 5'CCATTTTACAGTAGGAGGCTGG3' (SEQ ID NO:9);
ADU2R, 5'CTCTAGGGATCAGCACAGCC3' (SEQ ID NO:10);
ADU3F, 5'CAGGTCTGCTCTCCAGTTCC3' (SEQ ID NO:11);
ADU3R, 5'CTGTCCCCACCAGTGTGTC3' (SEQ ID NO:12);
ADU2aF, 5'CATCTGAGGCCCTCATGG3' (SEQ ID NO:13);
ADU2aR, 5'GCAGCACTGCTTATGCAGAG3' (SEQ ID NO:14);
der(2)F, 5'ATGAATCCAGGCAGATCTGG3' (SEQ ID NO:15);
der(2)R, 5'CTTTAATGAGCCCACCTCCA3' (SEQ ID NO:16);
der(22)F, 5'GGTGGCTTTTCCAGGTGTTA3' (SEQ ID NO:17);
der(22)R, 5'CTCTAGGGATCAGCACAGCC3' (SEQ ID NO:18);
CH2F, 5'GGTGGCTTTTCCAGGTGTTA3' (SEQ ID NO:17);
CH2R, 5'ACTGGAGGCTCTGCAAGGTA3' (SEQ ID NO:19);
BPC2F, 5'TACCTTGCAGAGCCTCCAGT3' (SEQ ID NO:20);
BPC2R, 5'GAAGGGCCAGAAGATAGATGG3' (SEQ ID NO:21);
22-cSTS2F, 5'GAGAAACATACAAATCAGGCCC3' (SEQ ID NO:22);
22-cSTS2R, 5'ACGTGTTTACTCGAGAGTGTGA3' (SEQ ID NO:23);
nex2.2-3F, 5'CTGTAGCAACACCAACTTCTGC3' (SEQ ID NO:24);
nex2.2-3R, 5'TAGCTCGAGGTGTTGGGC3' (SEQ ID NO:25);
pf12-rnex40F, 5'TGGACTCTCTCCTGCACCTT3' (SEQ ID NO:26); and
pf12-rnex40R, 5'CAGGTCAGTGCATGTGTGC3' (SEQ ID NO:27).

RT-PCR cDNA was synthesized in a 40 μl reaction using 1 μg of poly A$^+$ RNA extracted from various tissues. The RNA was heated with random and oligo(dt) primers for 10 minutes at 65° C. and cooled to room temperature. Reverse transcription was performed at 42° C. for 1 hour after adding 8 μl 5×RT buffer (Invitrogen), 20 U of RNAse inhibitor (Invitrogen), 2 μl of 0.1M dNTPs, 2 μl of 80 mM sodium pyrophosphate, and 10 U AMV reverse transcriptase. After 1 hour, a second aliquot of AMV Reverse Transcriptase (10 U) was added and incubation was continued for another hour. The cDNA was purified by phenol-chloroform extraction, ethanol precipitated and resuspended in 20 μl TE. For PCR amplification, 2 μl of cDNA was used per 20 μl reaction.

Northern Blot Analysis

Multiple tissue northern blots (Clontech) were hybridized to radiolabeled PCR products or purified inserts from cDNA clones at 65° C. in hybridization buffer, as described by Church and Gilbert, *Proc. Natl. Acad. Sci., USA*, 81:1991–1995, 1984, for 24 hours. Filters were washed in 2×SSC, 0.1% SDS at room temperature and then in 0.1× SSC, 0.1% SDS at 65° C. twice for 15–20 minutes each.

EXAMPLE 9

Polymorphism and Dosage Analysis

RFLP and/or dosage analysis of the translocation proband (ADU) and her mother (VDU) were performed using markers within and flanking the DGCR. ADU and VDU were found to be heterozygous at loci D22S9, D22S36 (pH11), D22S259 (R32) and D22S10. Dosage analysis for D22S75 (N25), a locus deleted in all DGS patients with interstitial deletions, demonstrated dizygosity in both individuals. Together, these loci span a distance of over 10 Mb in 22q11.2, encompass the DGCR, and failed to detect a deletion within or flanking the DGCR in ADU or VDU.

To rule out uniparental disomy as being responsible for the more severe phenotype of the proband (ADU), biparental origin of chromosome 2 and 22 loci was determined. Two simple tandem repeat polymorphisms (STRPs), D2S131 and D22S301, were tested on DNA from the proband (ADU) and her mother (VDU). Both ADU and VDU are heterozygous at D2S131 and D22S301. However, they share only one allele at each locus, indicating inheritance of paternally derived alleles on 2 and 22 in ADU (data not shown). Together with the cytogenetic findings, this demonstrated that the proband inherited only the der(2) and der(22) from her mother, and rules out the possibility that her "partial" DGS phenotype is the result of uniparental disomy.

EXAMPLE 10

Positioning the Breakpoint by Fluorescence In Situ Hybridization (FISH)

Figure 2A:
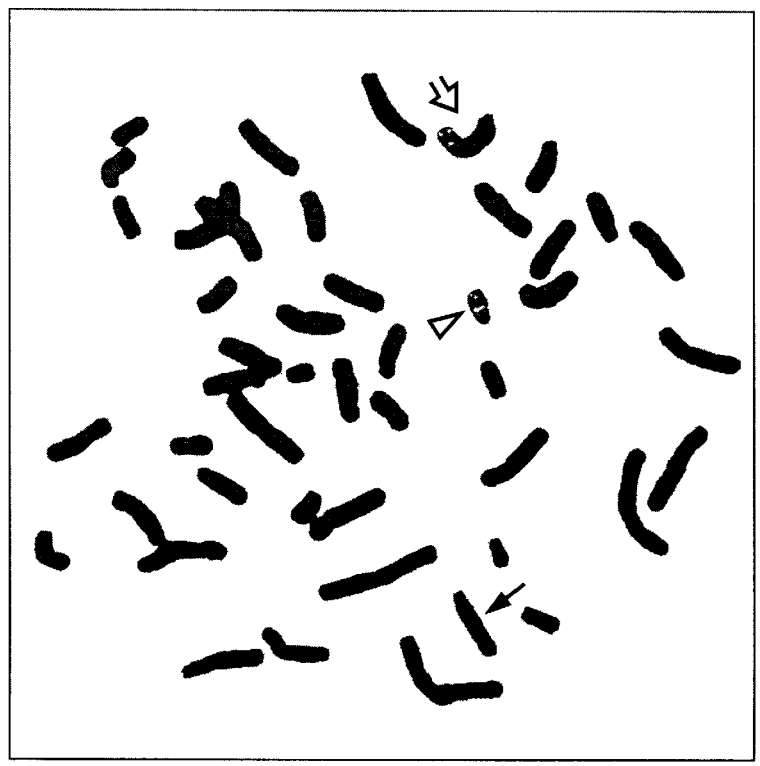
FIGS. 2A–2B depicts fluorescence in situ hybridization of chromosome 22 cosmids to metaphase chromosomes from ADU.

To position the translocation breakpoint within the region, FISH studies using cosmids containing ordered loci within the DGCR were undertaken. We described a commonly deleted region in 22q11.2 which is flanked on the centromeric side by pH11 (D22S36) and includes the region from D22S75 (N25) (centromeric) to D22S259 (R32) distally above. Using a cosmid probe for N25 (ONCOR, Gaithersburg Md.) and FISH to metaphase chromosomes from the ADU cell line, it was determined that N25 is translocated to the der(2) chromosome (FIG. 2a), demonstrating that the translocation breakpoint on chromosome 22 is proximal to D22S75. In FIG. 2, an arrowhead indicates the normal 22, an open arrow the der(2), and a solid arrow the der(22) chromosomes. Additional hybridizations with cosmids from a contig between D22S75 and D22S36 were undertaken, proceeding in a centromeric direction from D22S75.

A gridded, chromosome 22-only, cosmid library (LL22NC03) was screened by colony hybridization using a labeled 3.3 kb SacII-SfiI fragment, derived from the most centromeric cosmid in the N25 contig. Forty-five cosmids were identified in the primary screen which is six times higher than expected, suggesting that the probe contained duplicated sequences. Four of the cosmids had been previously identified by a N25 YAC screen of the same cosmid library and these were chosen for further analysis. Cosmid DNA was then digested with HindIII, Southern blotted and hybridized with the 3.3 kb probe to verify the positive. All four cosmids gave positive signal and were further restriction mapped to order them with respect to the cosmid contig.

Figure 2B:

The cosmid 39G4 extended the furthest proximally and appeared to contain the breakpoint as signal was detected on both of the derivative chromosomes (FIG. 2b). Cosmids distal to and overlapping with 39G4 in the contig hybridized only to the der(2). Cosmid D22S39 (pH17) (Oncor) maps to the distal long-arm of chromosome 22 and was used as a control probe to identify the chromosome 22s in metaphase spreads. Metaphase spreads prepared from peripheral blood lymphocytes or lymphoblastoid cell lines from ADU were cohybridized with biotinylated-11-d-UTP labeled test probe and the control probe and visualized with fluoresceinated avidin (Greenberg et al., *J. Med. Genet.*, 30:803–806, 1993).

EXAMPLE 11
Identification of Rearranged Fragments Using a cDNA

The 39G4 cosmid was used to screen a fetal brain cDNA library to identify a gene(s) in the vicinity of the translocation breakpoint. A 2.5 kb partial cDNA was identified (hereinafter referred to as LAN). On Northern blot analysis, this cDNA detected a 4.5 kb transcript which was detected in all tissues tested (heart, brain, placenta, lung, liver, skeletal muscle, kidney, pancreas) (shown as a control in FIG. 8d).

This cDNA was used as a probe to Southern blots of genomic DNA prepared from ADU and VDU cell lines. Novel rearrangement fragments in EcoRI and HindIII digested DNA samples were detected (FIG. 3). Lanes 1 and 4 contain total human DNA, lanes 2 and 5 contain ADU DNA and lanes 3 and 6 contain VDU DNA. For the EcoRl digests, the 15 kb band is derived from the normal chromosome 22 and the 22 kb rearranged band from the der(2) in ADU and VDU. Restriction digestion with HindIII produces a normal 18 kb band and a rearranged 16.5 kb band seen only in ADU and VDU.

Although these novel bands could represent DNA polymorphisms, the positioning of the breakpoint in this region makes it more likely that the rearrangement occurs within a 15.0 kb EcoRI fragment which contains the LAN cDNA.

The LAN cDNA was sequenced and found to contain a poly-A tail, allowing orientation of the transcript with respect to the breakpoint. The results of these analyses demonstrate that the corresponding gene is in the vicinity of the breakpoint, but is not disrupted by it. Its 3' end is distal to the breakpoint, and transcription of this gene is directed telomere (5') to centromere (3') (See FIG. 4a).

EXAMPLE 12
Narrowing the Location of the Translocation Breakpoint

A complete contig of the DGCR was constructed and is in the process of being sequenced in its entirety. Over 250 kb of genomic sequence has been generated in the proximal DGCR including a cosmid 46A9 which spans the ADU breakpoint. Using restriction map information generated from analysis of the cosmid sequence, several PCR-derived probes in repeat free regions were generated (FIG. 4a). In FIG. 4a, the top line represents 25 kb of chromosome 22 genomic DNA in the region of the breakpoint. The restriction enzymes are abbreviated as follows: B-BamHI, H-HindIII, R-EcoRI, S-Sac1 and T-Taq1.

The first of the probes, ADU1, is a 846 bp PCR product located approximately 5.0 kb centromeric to the 3' end of LAN. This probe picks up the same HindIII and EcoRI rearrangement fragments as LAN when used as a probe against Southern blots of ADU and VDU genomic DNA, indicating it is on the same side of the breakpoint.

The second probe, ADU2, is a 670 hp PCR product which is located approximately 8.0 kb centromeric to the 3' end of LAN. In addition to the same rearrangement fragments detected by LAN and ADU1, ADU2 hybridized to faint, novel, fragments in the ADU and VDU samples digested with BamHI and EcoRI. These results suggested that ADU2 may span the breakpoint.

The third probe, ADU3, is a 830 hp PCR product which is located approximately 9.5 kb centromeric to the 3' end of LAN. Southern hybridization of ADU1 VDU genomic DNA using this probe indicated new HindIII and EcoRI bands, suggesting that it is on the other side of the breakpoint. The size of the novel EcoRI fragment was the same as the faint band detected by ADU2.

The position of the ADU1, ADU2, and ADU3 probes used to identify the breakpoint are shown above the line in FIG. 4a and the position of the cDNA, LAN, is indicated below. The breakpoint is identified by the vertical wavy line. The broken arrows indicate an enlarged view of the breakpoint region. Also shown is the position of the probe ADU2A, described below.

A restriction map was generated from the genomic sequence to select enzymes with sites closely flanking the putative breakpoint. SacI and TaqI were chosen initially. The experimental results from Southern blot analysis using the enzymes SacI and TaqI are shown in FIG. 5. The lanes in FIGS. 5a–c are as follows: (1 and 5) GM10888 chromosome 22 only somatic cell human-hamster hybrid; (2 and 6) normal male control; (3 and 7) ADU (affected proband); (4 and 8) VDU. Normal (germline) 2.0 kb (SacI) and 2.2 kb (Taql) fragments are present in all lanes.

The ADU2 probe (FIG. 5a) detects two novel fragments in the ADU and VDU samples with either SacI or TaqI. Asterisks indicate the two novel bands (6.5 kb and 2.2 kb SacI; 3.7 kb and 2.5 kb TaqI) recognized by the ADU2 probe in DNA from the translocation carriers (lanes 3 and 7 ADU; lanes 4 and 8 VDU) as a result of the rearrangement. These novel fragments are not seen in the total human control (lanes 2 and 6) or GM10888, the chromosome 22-only hybrid (lanes 1 and 5). These results provide further evidence that the ADU2 probe spans the t(2;22) breakpoint.

Further, at the level of resolution of agarose gel electrophoresis, VDU has the same rearranged fragments as ADU.

To further test this possibility a second PCR probe, ADU2A, was designed that is specific to the distal region of ADU2 (See FIG. 4a). ADU2A recognizes only one of the two novel fragments in each digest, supporting the hypothesis that the ADU2 fragment crosses the breakpoint (FIG. 5b). The same normal fragments are present in all lanes but only one of the novel fragments (6.5 kb SacI; 2.5 kb TaqI) are present (asterisks) in ADU or VDU DNA indicating that this probe recognizes only one side of the translocation.

EXAMPLE 13

Cloning the der(2) Translocation Breakpoint

Figure 6:
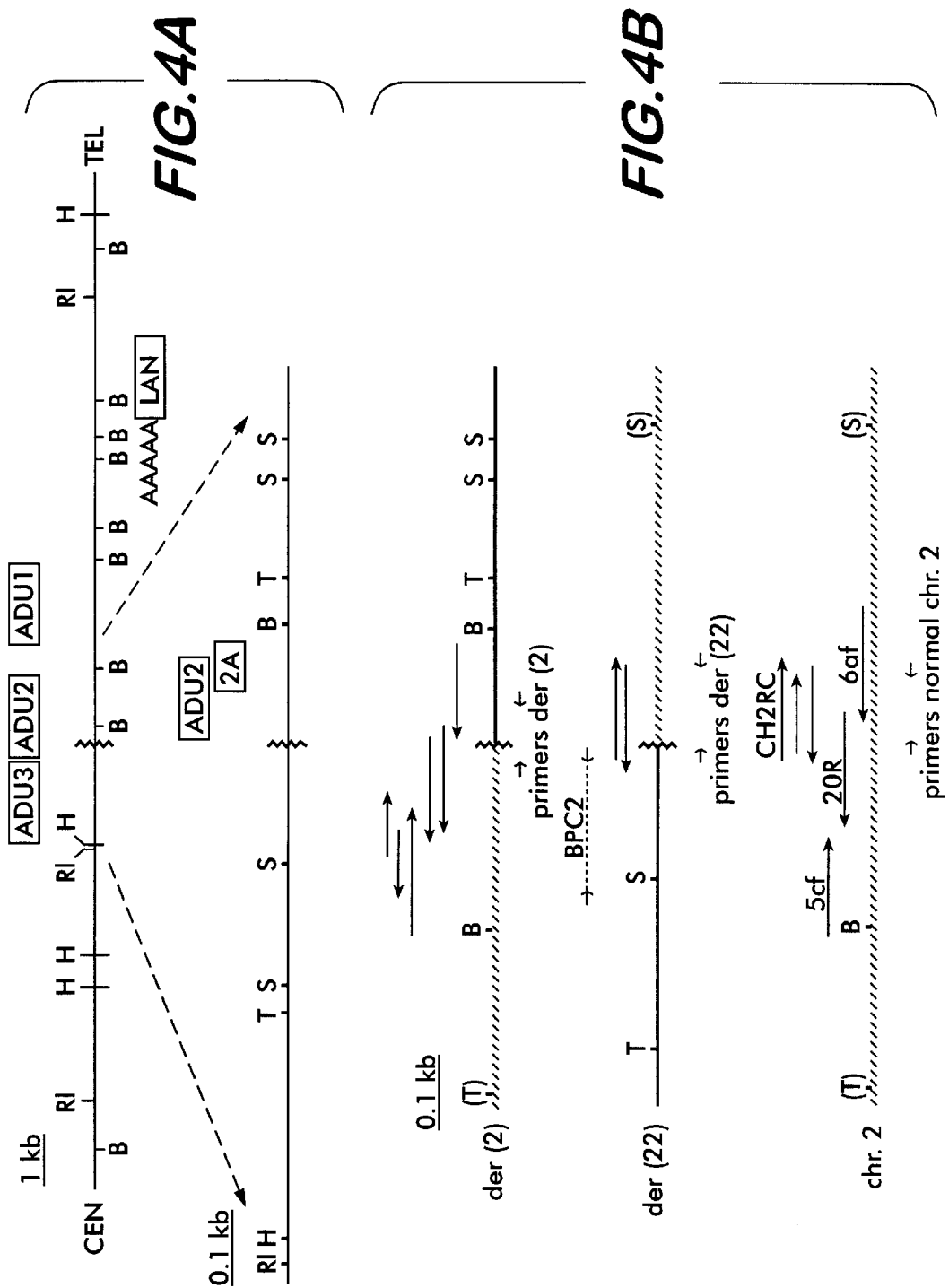
FIGS. 6A–6C depicts the sequences of the t(2;22) translocation chromosomes.

In addition to SacI and TaqI, which revealed rearranged fragments when probed with ADU2 (FIG. 5a), BamHI detected a novel 1.5 kb fragment in the translocation carriers, as well as the normal 11.5 kb band. Hybridization experiments using ADU2A demonstrated that this 1.5 kb band corresponded to the der(2) side of the rearrangement (see FIG. 4a). This fragment was preparatively isolated on an agarose gel and cloned into Lambda Zap ExpressTM (Stratagene). The library was screened with the ADU2 probe. Three phage clones (clones 5, 6B and 10, respectively) out of several positives were isolated from the library and subjected to DNA sequencing. The sequencing of all three clones revealed identity with the 46A9 cosmid sequence starting from the BamHI site to 547 bp downstream, at which point sequence no longer matched that of the breakpoint-containing cosmid (see FIGS. 6b, 6c). The cosmid was sequenced by a double stranded random shotgun approach as previously described (Chissoe et al., *Methods: Companion Methods Enzymol.,* 3: 55–65, 1991; Bodenteich et al., *Automated DNA Sequencing and Analysis Techniques,* J. C. Venter, Ed., pp.42–50, Academic Press, London, 1993; Chissoe et al., *Genomics,* in press, 1995). The breakpoint region is indicated in FIG. 6b by the shaded nucleotides and the single nucleotide in the small box. The large block of boxed nucleotides represents the rnex4O ORF predicted by GRAIL 1a.

The two derivative chromosomes and the normal chromosome 2 are diagrammatically displayed in FIG. 4b. The solid horizontal lines represent portions of chromosome 22 and the stippled horizontal lines portions of chromosome 2 in the region of the breakpoint. Lines with arrows at one end represent the direction and extent of the sequencing runs. Arrowheads indicate the position of primers used. 5cF, 2OR and 6aF refer to phage clones used for end sequencing. Parentheses around restriction sites indicate that they were derived from Southern blotting experiments. All others were derived from sequence data.

PCR primers (BPC2) (FIG. 4b) were selected from the novel sequence and used to amplify a 638 bp product. BPC2 was used to screen the normal phage library. This PCR product was hybridized to the SacI/TaqI Southern blot previously described and the results are shown in FIG. 5c. The same size rearrangement fragments of 6.5 kb (SacI; lanes 3 and 4) and 2.5 kb (TaqI; lanes 7 and 8) as are seen upon probing with ADU2 or ADU2A are recognized in ADU and VDU samples. However, the normal fragments were different, indicating that the BPC2 sequence is not normally contiguous with ADU2. These results suggested that the novel sequences in the 1.5 kb BamHI fragment are derived from chromosome 2 in the region of the breakpoint. Further, the BPC2 probe appears to detect non-22 conserved sequences in the hamster, as seen in the chromosome 22 only hybrid (lanes 1 and 5, inverted triangles), suggestive of a gene near the breakpoint on the chromosome 2 side. The chromosome 2 related germline bands are of a distinct and different size from the chromosome 22 germline fragments seen in panels a and b.

PCR primers [(der(2)F and der(2)R)] flanking the breakpoint were selected and used to PCR amplify DNA samples from ADU, VDU, normal human, a chromosome 2 only hybrid and a chromosome 22 only hybrid. Only ADU and VDU amplified the expected 490 bp product. The PCR product for VDU was purified, sequenced and compared to the ADU sequence. 438 bp of sequence was obtained from the VDU der(2), including the breakpoint region, and there are no mismatches with the sequence of the ADU der(2). Thus, there are no sequence changes at the der(2) breakpoint region between ADU and VDU.

Subregional localization of the chromosome 2 portion of the cloned, ADU translocation fragment was accomplished using the 1.5 kb BamHI insert. The 1.5 kb, rearranged BamHI fragment was isolated from one of the phage clones (clone 5), radiolabeled, and used as a probe against DNA from a control and a somatic cell hybrid panel containing regions of chromosome 2 digested with HindIII: GM10826B is a somatic cell hybrid containing human chromosome 2 as its only human material; 23-2 is a human X/hamster fusion containing the der(20) of a t(2;20)(q21.3;p12) (Spinner et al., *Am. J. Hum. Genet.,* 55:238–243, 1994); HC10 contains the der(2) from a t(X;2) (q13.2;q32) (Verga et al., *Am. J. Hum. Genet.,* 48:1133–1137, 1991); and GM11022 contains the der(X) of a t(X;2)(p21;q37). Signal was present in GM10826B and HC10 which contain all of chromosome 2 and 2pter-q32, respectively. Signal was absent from hybrids 23-2 and GM11022, which contain 2q21-qter and 2q36-qter, respectively. From this analysis it was concluded that the 1.5 kb BamHI fragment is the ADU translocation junction since one side maps to chromosome 22 and the other to chromosome 2 in the region pter-q21.3.

EXAMPLE 14

Cloning the Normal Chromosome 2 Sequences in the Region of the Breakpoint

Figure 7:
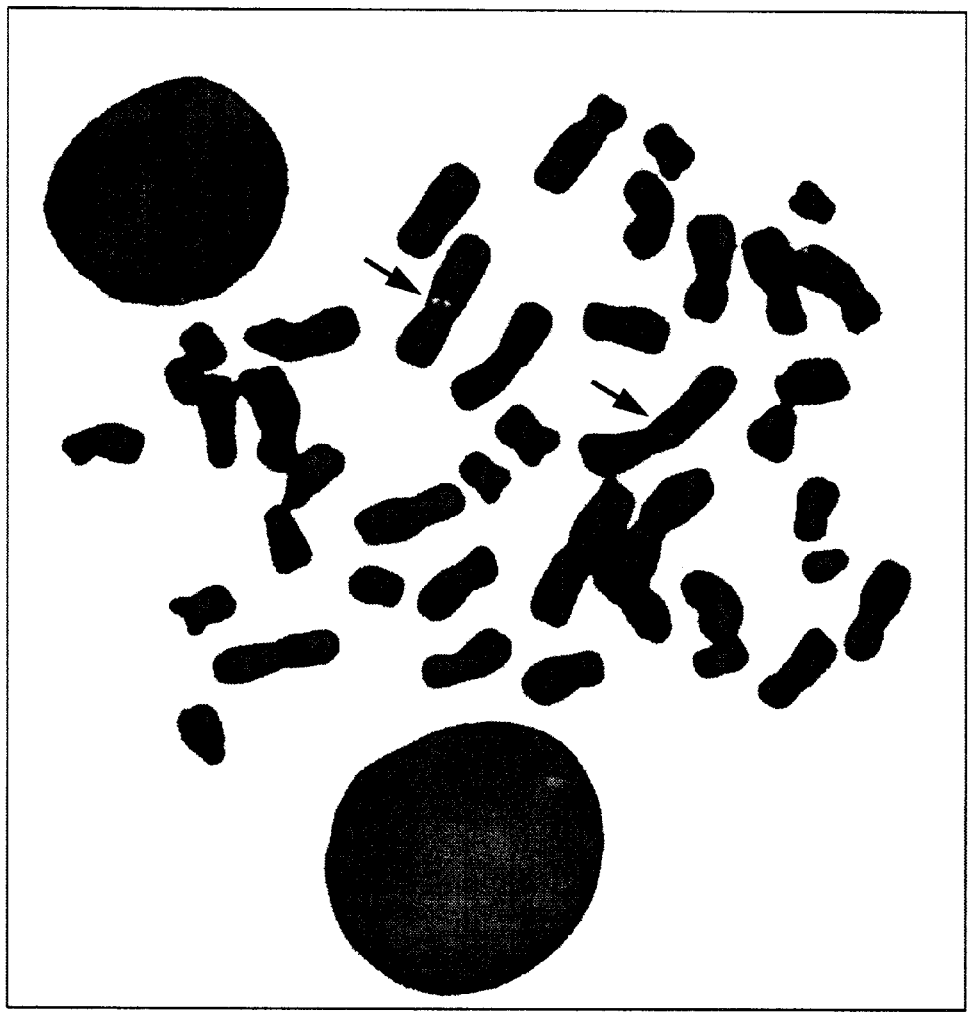
FIG. 7 depicts fluorescence in situ hybridization mapping of the chromosome 2 translocation partner.

To determine if the ADU translocation is balanced, it was necessary to characterize the normal sequences from chromosome 2 and 22, as well as both sides of the breakpoint. To obtain material from the normal chromosome 2, the 628 bp PCR product (BPC2), derived from chromosome 2 specific sequences within the 1.5 kb BamHI rearrangement fragment, was used to screen a normal, unamplified, human genomic phage library. Eight positive clones were identified after secondary screens and all eight were isolated for analysis. FISH analysis of two of these clones, one of which is shown (FIG. 7), verified that they mapped to 2q14. In FIG. 7, the hybridization of this clone, clone 5, which contains the breakpoint region to normal metaphase chromosomes, is depicted. The arrow indicates hybridization to 2q14.

A primer to the reverse strand of the der(2) (CH2RC) (FIG. 4b) was designed using chromosome 2 sequence immediately adjacent to the breakpoint allowing sequencing across the breakpoint region on the normal chromosome 2 (FIG. 6c). This primer was used to directly sequence the phage DNA and provided 465 bp of novel chromosome 2 sequence on the distal side of the breakpoint. The sequence is presented in FIG. 6c. In FIG. 6c, the sequence in plain type is sequence from chromosome 2, including the portion translocated to the der(22). The sequence in bold type is from chromosome 22, including the portion translocated to the der(2). The nucleotides displayed in lower case letters are lost as a result of the translocation. The shaded areas indicate sequence at the breakpoint which has been lost by one, but not both of the partners. The two different blocks of nucleotides with a stippled overline are present on chromosome 2 and chromosome 22 upstream of the breakpoint. The bold underline indicates nucleotides repeated on chromosomes 2 and 22 which, in some combination, are lost at the breakpoint.

PCR primers which flanked the breakpoint region (CH2F and CH2R) were then used to PCR amplify a 495 hp fragment from three, independently isolated, chromosome 2 phage clones. Additional sequence was obtained by sequencing the ends of normal genomic phage clones which contained the breakpoint region (McDermid et al., Genomics, 5:1–8, 1989) and the sequence derived from chromosome 2 was assembled into a 1483 bp contig (FIG. 6a). In FIG. 6a, the breakpoint region is indicated by the shaded and boxed nucleotides.

EXAMPLE 15

Cloning the der(22) Translocation Breakpoint

A PCR-based approach was employed to obtain material for DNA sequencing from the breakpoint region on the der(22). Using the normal chromosome 2 and 22 sequences, primers were selected which would flank the der(22) breakpoint region [der(22)F and der(22)R]. These primers amplified the predicted 520 bp product from DNA samples of ADU and VDU, but not from a normal human control or chromosome 2 or 22 only hybrid DNA samples. The PCR products from both ADU and VDU samples were isolated and sequenced. As was the case for the der(2), there were no mismatches between the ADU and VDU sequences within the 455 bp region of the der(22) for which we obtained sequence.

EXAMPLE 16

Identification of DGS Candidate Genes

Several methods were used for transcript identification including GRAIL analysis, exon amplification and cDNA selection. In the region surrounding the breakpoint, approximately 5 kb, there are four excellent exons predicted by GRAIL (Uberbacher et al., Proc. Natl. Acad. Sci. U.S.A., 88:11261–11265, 1991), two on each strand (FIG. 8a): nex2.2, nex3, rnex39 and rnex4O. Also depicted are ac2bl—a clone isolated by cDNA selection (Gong et al., Am. J. Hum Genet., 55:A259, 1994); and pfl2—a clone identified by exon amplification (Church et al., Nature Genet., 6:98–105, 1994; Nisson et al., Current Protocols in Human Genetics, Volume I, Dracapoli, N. C., et al., eds., pp. 6.1.1–6.1.14, John Wiley and Sons, N.Y., 1994). By inter-exon RT-PCR of skeletal muscle cDNA (using primers nex2.2-3R and nex2.2-3F) it was possible to demonstrate that nex2.2 and nex3 are part of the same transcript, amplifying a 145 bp product in the cDNA and a 230 bp product in genomic DNA. Further, hybridization of the nex2.2-nex3 PCR product to a multi tissue northern blot detected a 1.6 kb message in several tissues with strongest signal in heart and skeletal muscle (FIG. 8b). ac2bI, a cDNA isolated by cDNA selections (using primers 22-cSTS2F and 22-cSTS2R), maps centromeric to nex2.2-nex3 and detects a transcript of similar size and tissue distribution (FIG. 8b). A FASTA similarity search did not detect any sequence similarity between these two regions, indicating that the observed bands are not due to cross-hybridization. Efforts to obtain full length transcripts for nex2.2-nex3 and ac2b1 are in progress, in order to determine if they are part of the same gene. BLAST searches of the nucleotide and protein databases did not reveal similarity to previously identified genes.

As a control to the blot in panel c, the same northern blot was probed using the LAN cDNA, demonstrating that the same amount of mRNA was loaded in each lane. A 4.5 kb message is detected in all tissues, demonstrating the presence of RNA in all lanes (FIG. 8d).

On the opposite strand, there are three putative exons in the region of the breakpoint. None of these recognize previously identified sequences in the nucleotide or protein databases. A 180 bp GRAIL predicted open reading frame (ORF), rnex4O, spans the breakpoint and is disrupted by the translocation. PCR primers to rnex4O were selected and used to amplify a 124 bp product from skeletal muscle cDNA. Since these primers are within the same exon, the size of the PCR product is the same in genomic as in cDNA. To control for this, the skeletal muscle cDNA was tested with multiple primer pairs for transcripts within the DGCR which distinguish cDNA from genomic. The cDNA was found to be free of genomic contamination, indicating that rnex4O primers are detecting a bona fide transcript. A 3' RACE using a pair of nested primers, within rnex4O, was performed. A 1.0 kb product was amplified and sequence analysis demonstrated 97.3% identity over the 367 bp sequenced. PCR primers for the GRAIL predicted ORF, rnex39, were also selected. However, the CG content of this predicted ORF is very high and the primers did not amplify a discrete product of the expected size. A 119 bp fragment identified by exon amplification (Church et al., supra, and Nisson et al., supra), pf12, is located 244 bp upstream of rnex4O. This "trapped exon" was not predicted by GRAIL.

RT-PCR between pf12 and rnex4O (primers pf12-rnex4OF and pf12-rnex40R) produced an approximately 500 bp product using skeletal muscle cDNA. The same size product was observed using total human DNA, indicating absence of introns. Sequence analysis of this RT-PCR product confirmed that it is derived from pf12-rnex4O. These RT-PCR results suggest that alternative exon splicing, different from the GRAIL prediction, may occur in skeletal muscle. Further, when this RT-PCR product is used as a probe on Northern blots (FIGS. 8e,f), multiple transcripts in adult and fetal tissues are identified. A 1.5 kb message is detected in varying abundance in all tissues. A 2.2 kb transcript is detected only in fetal and adult liver. Finally, a 5.7 kb transcript is found in adult heart, skeletal muscle and liver, as well as in fetal liver.

The pf12-rnex40 cDNA sequence represents an open reading frame of about 782, encoding 260 amino acids (FIG. 9a). The chromosome 2 sequence translocated into this region introduces a stop codon 61 nucleotides downstream of the breakpoint and replaces the last 89 amino acids of the normal protein with 20 new amino acids (shaded region in FIG. 9a). We used the normal amino acid sequence predicted from this ORF to search peptide sequence (NCBI nrdb) and pattern (ProSite, BLOCKS, and CRseq) databases. Searches of the ORF using BLAST and BEAUTY identified weak similarity to rat and mouse androgen receptor sequences. Using PileUp, we generated a four-way alignment of sequence from this ORF with human, mouse, and rat androgen receptors (FIG. 9b). The regions of similarity are localized to the N-terminal trans-activation domain of the androgen receptors and do not extend into the DNA-binding or steroid-recognition domains. As shown by the triangles in FIG. 8b, there is a potential leucine zipper motif at the N-terminus of the rnex40 sequence. Several of these leucines are conserved between rnex40 and the androgen receptor sequence. However, the spacing of the leucines in the androgen receptor is not consistent with a leucine zipper.

The t(2;22) breakpoint occurs (large asterisk, FIG. 9b) within the androgen receptor homologous region and separates the last cluster of conserved residues from the more N-terminal portion of the polypeptide. These comparisons indicate only limited similarity. Nonetheless, similarity to members of a family of transcriptional regulators could suggest a role for the rnex40 gene product consistent with the developmental phenotype of the DiGeorge syndrome.

EXAMPLE 17

Deletion of the DGS Candidate Genes in DGS/VCFS Patients

To assess whether deleted patients are haploinsufficient for this region, DGS/VCFS patients with interstitial deletions and unbalanced translocations of 22q11 were studied. Nine patients with interstitial deletions encompassing the N25 cosmid (Oncor) were studied by FISH with a cosmid for the flanking locus D22S36 (pH11). D22S36 maps less than 100 kb proximal to the ADU/VDU breakpoint. Hybridization signal to only one homolog was observed in each patient, indicating a deletion of locus D22S36. Hence, the upper boundary of the 22q11 interstitial deletion in 9/9 patients studied extends proximally, beyond the t(2;22), and results in hemizygosity for the DGS candidate loci. Southern blot analysis of 4 additional DGS patients identified deletions which extend proximally to D22S36 (Driscoll et al., 1992, supra, and Budarf et al., in press, supra). Further, we have positioned the breakpoints of nine DGS/VCFS associated unbalanced translocations within 22q11 (Li et al., *Am. J. Hum. Genet.*, 55:A10, 1994). All are distal to the t(2;22), indicating that the DGS/VCFS unbalanced rearrangements result in the loss of these DGS candidate loci. The most proximal of these breakpoints is a t(X;22), located less than 20 kb distal to the t(2;22), adding further significance to the genes in this region.

What is claimed is:

1. A method of detecting genetic deletions and mutations associated with at least one condition selected from the group consisting of DiGeorge syndrome, Velocardiofacial syndrome, CHARGE association, conotruncal defect and cleft palate in a human patient comprising the steps of:
   providing a DNA containing test sample from said human patient; and
   identifying whether there are less than two functional copies of the region of chromosome 22q11 from and including the locus D22S36 to the locus BCRL2;
   whereby said identification of less than two functional copies of said region is indicative of a likelihood that said person has a genetic deletion or mutation associated with at least one of DiGeorge syndrome, Velocardiofacial syndrome, CHARGE association, conotruncal cardiac defect and cleft palate.

2. A method of detecting a genetic translocation associated with at least one condition selected from the group consisting of DiGeorge syndrome, Velocardiofacial syndrome, CHARGE association, conotruncal defect and cleft palate in a human patient comprising the steps of:
   providing a DNA containing test sample from said human patient; and
   identifying whether said test sample hybridizes with a probe directed to the region of chromosome 22q11 between the loci D22S36 and D22S75;
   identifying whether said hybridization is with chromosome 22 of the test sample;
   whereby hybridization with a chromosome other than chromosome 22 is indicative of a likelihood that said person has a genetic translocation associated with at least one of DiGeorge syndrome, Velocardiofacial syndrome, CHARGE association, conotruncal cardiac defect and cleft palate.

3. A method of detecting a genetic translocation associated with at least one condition selected from the group consisting of DiGeorge syndrome, Velocardiofacial syndrome, CHARGE association, conotruncal defect and cleft palate in a human patient comprising the steps of:
   providing a DNA containing test sample from said human patient; and
   hybridizing a probe directed to the region of chromosome 22q11 in which the breakpoint for t(2;22)(q14;q11.21) occurs;
   identifying whether said hybridization occurs with more than one chromosome of the test sample;
   whereby hybridization with more than one chromosome is indicative of a likelihood that said person has a genetic translocation associated with at least one of DiGeorge syndrome, Velocardiofacial syndrome, CHARGE association, conotruncal cardiac defect and cleft palate.

4. A method of detecting a genetic translocation associated with at least one condition selected from the group consisting of DiGeorge syndrome, Velocardiofacial syndrome, CHARGE association, conotruncal defect and cleft palate in a human patient comprising the steps of:
   providing a DNA containing test sample from said human patient; and
   identifying whether said test sample hybridizes with a probe directed to the breakpoint region of chromosome der(2) or der(22);
   whereby hybridization is indicative of a likelihood that said person has a genetic translocation associated with at least one of DiGeorge syndrome, Velocardiofacial syndrome, CHARGE association, conotruncal cardiac defect and cleft palate.

5. A method of detecting genetic deletions and mutations associated with at least one condition selected from the group consisting of DiGeorge syndrome, Velocardiofacial syndrome, CHARGE association, conotruncal defect and cleft palate in a human patient comprising the steps of:

providing a DNA containing test sample from said human patient;

contacting a detectably labeled nucleic acid probe, said probe being substantially complementary to the region of chromosome 22q11 from and including the locus D22S36 to BCRL2, with said test sample under hybridizing conditions; and detecting hybridization of said detectably labeled probe with DNA of chromosome 22;

whereby the absence of hybridization of said detectably labeled probe is diagnostic of the likelihood said human has a genetic deletion or mutation associated with at least one of DiGeorge syndrome, Velocardiofacial syndrome, CHARGE association, conotruncal cardiac defect and cleft palate.

6. A method of detecting genetic deletions and mutations associated with at least one condition selected from the group consisting of DiGeorge syndrome, Velocardiofacial syndrome, CHARGE association, conotruncal defect and cleft palate in a human patient comprising the steps of:

providing a DNA containing test sample from said human patient; and identifying whether there are less than two functional copies of the region of chromosome 22q11 from and including the locus N25±0.5 megabases to and including the locus R32±0.5 megabases;

whereby said identification of less than two functional copies of said region is indicative of a likelihood that said person has a genetic deletion or mutation associated with at least one of DiGeorge syndrome, Velocardiofacial syndrome, CHARGE association, conotruncal cardiac defect and cleft palate.

7. A method of detecting genetic deletions and mutations associated with at least one condition selected from the group consisting of DiGeorge syndrome, Velocardiofacial syndrome, CHARGE association, conotruncal defect and cleft palate in a human patient comprising the steps of:

providing a DNA containing test sample from said human patient;

contacting a detectably labeled nucleic acid probe, said probe being substantially complementary to the region of chromosome 22q11 from and including the locus N25±0.5 megabases to and including the locus R32±0.5 megabases, with said test sample under hybridizing conditions; and detecting hybridization of said detectably labeled probe with DNA of chromosome 22;

whereby the absence of hybridization of said detectably labeled probe is diagnostic of the likelihood said human has a genetic deletion or mutation associated with at least one of DiGeorge syndrome, Velocardiofacial syndrome, CHARGE association, conotruncal cardiac defect and cleft palate.

8. The method of claim 5 or 7 wherein said probe is prepared using primers selected from the group consisting of 5'ACACTOGTCCACAGTGCCAG3' (SEQ ID NO:1); 5'TGTGAGGGCTTGCTCTGAGC3' (SEQ ID NO:2); 5'TGGTACCGCTGCTCAGAGGGC3' (SEQ ID NO:3); 5'TCCCAGCCTCTGGCCTGAGTG3' (SEQ ID NO:4); 5'CTAACACCTATCCTCCGCCG3' (SEQ ID NO:5); 5'GGCAGCAGGGAAACAGAAAC3' (SEQ ID NO:6).

9. The method of claim 4 wherein said probe is prepared using primers selected from the group consisting of der(2)R, 5'CTTTAATGAGCCCACCTCCA3' (SEQ ID NO:16); and der(22)F, 5'GGTGGCTTTTCCAGGTGTTA3' (SEQ ID NO:17).

10. A diagnostic kit for the detection of genetic deletions or mutations associated with at least one condition selected from the group consisting of DiGeorge syndrome, Velocardiofacial syndrome, CHARGE association, conotruncal cardiac defect, and cleft palate comprising primer pairs effective to amplify a region of chromosome 22q11 from and including the locus D22S36 to the locus BCRL2.

11. A diagnostic kit for the detection of genetic translocations associated with at least one condition selected from the group consisting of DiGeorge syndrome, Velocardiofacial syndrome, CHARGE association, conotruncal cardiac defect, and cleft palate comprising primer pairs effective to amplify the breakpoint region of der(2) or der(22).

12. The kit of claim 10 wherein the primer pairs are selected from the group consisting of der(2)R, 5'CTTTAATGAGCCCACCTCCA3' (SEQ ID NO:16); and der(22)F, 5'GGTGGCTTTTCCAGGTGTTA3' (SEQ ID NO:17).

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ACACTGGTCC ACAGTGCCAG       20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TGTGAGGGCT TGCTCTGAGC       20

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

TGGTACCGCT GCTCAGAGGG C       21

(2) INFORMATION FOR SEQ ID NO:4:

(i) SEQUENCE CHARACTERISTICS:
      (A) LENGTH: 21 base pairs
      (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:4:

TCCCAGCCTC TGGCCTGAGT G                                              21

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CTAACACCTA TCCTCCGCCG                                                20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGCAGCAGGG AAACAGAAAC                                                20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CACCGTGCTC TGCTAAATGA                                                20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCTCTGAGTC AAAAGGGTGC                                                20

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCATTTTACA GTAGGAGGCT GG                                         22

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTCTAGGGAT CAGCACAGCC                                            20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CAGGTCTGCT CTCCAGTTCC                                            20

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CTGTCCCCAC CAGTGTGTC                                             19

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CATCTGAGGC CCTCATGG                                              18

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCAGCACTGC TTATGCAGAG                                            20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

ATGAATCCAG GCAGATCTGG                                            20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CTTTAATGAG CCCACCTCCA                                            20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGTGGCTTTT CCAGGTGTTA                                            20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CTCTAGGGAT CAGCACAGCC                                            20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ACTGGAGGCT CTGCAAGGTA                                            20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TACCTTGCAG AGCCTCCAGT                                               20

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GAAGGGCCAG AAGATAGATG G                                             21

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GAGAAACATA CAAATCAGGC CC                                            22

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ACGTGTTTAC TCGAGAGTGT GA                                            22

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTGTAGCAAC ACCAACTTCT GC                                            22

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single -continued

```
        (D) TOPOLOGY: linear (ii) MOLECULE TYPE: DNA (genomic)

(xi) SEQUENCE DESCRIPTION: SEQ ID NO:25:

TAGCTCGAGG TGTTGGGC                                                        18

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TGGACTCTCT CCTGCACCTT                                                      20

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CAGGTCAGTG CATGTGTGC                                                       19
```